US005869304A

United States Patent [19]
Dickson et al.

[11] Patent Number: 5,869,304
[45] Date of Patent: Feb. 9, 1999

[54] TECHNIQUE FOR SPECIFYING THE FATTY ACID AT THE SN2 POSITION OF ACYLGLYCEROL LIPIDS

[75] Inventors: Robert C. Dickson; Robert L. Lester; M. Marek Nagiec, all of Lexington, Ky.

[73] Assignee: University of Kentucky Research Foundation, Lexington, Ky.

[21] Appl. No.: 321,670

[22] Filed: Oct. 12, 1994

[51] Int. Cl.$^6$ .......................... C12N 15/63; C07H 21/04
[52] U.S. Cl. ...................... 435/172.3; 536/23.2; 536/24.3
[58] Field of Search .................. 435/69.1, 91.1, 435/91.4, 172.3, 320.1; 514/44; 536/23.2, 23.74, 24.1, 24.3, 25.32; 935/8, 23, 28, 34, 35, 37

[56] References Cited

U.S. PATENT DOCUMENTS

| | | | |
|---|---|---|---|
| 5,057,419 | 10/1991 | Martin et al. | 435/134 |
| 5,286,633 | 2/1994 | Moore | 435/134 |
| 5,288,619 | 2/1994 | Brown et al. | 435/134 |

OTHER PUBLICATIONS

Hakomori, S. (1983) in *Handbook of Lipid Research* (Kanfer, J.N., and Hakamori, S., eds) vol. 3, pp. 1–165, Plenum Publishing Corp., New York.
Hannun, Y.A., and Bell, R.M. (1989) *Science*, vol. 243, pp. 500–507.
Hakomori, S. (1990) *J. Biol. Chem.*, vol. 265, pp. 18713–18716.
Smith, S.W., and Lester, R.L. (1974) *J. Biol. Chem.*, vol. 249, pp. 3395–3405.
Steiner, S., Smith, S., Waechter, C.J., and Lester, R.L. (1969) *Proc. Natl. Acad. Sci. U.S.A.*, vol. 64, pp. 1042–1048.
Merrill, A.H., Jr., and Jones, D.D. (1990) *Biochim. Biophys Acta.*, vol. 1044, pp. 1–12.
Buede, R., Rinker–Schafer, C., Pinto, W.J., Lester, R.L., and Dickson, R.C. (1991) *J. Bacteriol.*, vol. 173, pp. 4325–4332.
Wells, G.B., and Lester, R.L. (1983) *J. Biol. Chem.*, vol. 258, pp. 10200–10203.
Pinto, W.J., Srinivasan, B., Shepherd, S., Schmidt, A., Dickson, R.C., and Lester, R.L. (1992) *J. Bacteriol.*, vol. 174, pp. 2565–2574.
Pinto, W.J., Wells, G.W., and Lester, R.L. (1992) *J. Bacteriol.*, vol. 174, pp. 2575–2581.
Dickson, R.C., Wells, G.B., Schmidt, A., and Lester, R.L. (1990) *Mol. Cell. Biol.*, vol. 10, pp. 2176–2181.
Lester, R.L., Wells, G.B., Oxford, G., and Dickson, R.C. (Jan. 15, 1993) *J. Biol. Chem.*, vol. 269, pp. 845–856.
Coleman, J. (1992) *Mol. & Gen. Genet.*, vol. 232, pp. 295–303.
Strathern, J.N., and Higgins, D.R. (1991) *Methods Enzymol.*, vol. 194, pp. 319–329.
Ma, H., Kunes, S., Schatz, P.J., and Botstein, D. (1987) *Gene (Amat.)*, vol. 58, pp. 201–216.
Stiles, J.I., Szostak, J.W., Young, A.T., Wu, R., Consaul, S., and Sherman, F. (1981) *Cell*, vol. 25, pp. 277–284.

Sikorski, R.S., and Hieter, P. (1989) *Genetics*, vol. 122, pp. 19–27.
Carlson, M., and Botstein, D. (1982) *Cell*, vol. 28, pp. 145–154.
Kuzhandaivelu, N., Jones, W.K., Martin, A.K., and Dickson, R.C. (1992) *Mol. Cell. Biol.*, vol. 12, pp. 1924–1931.
Barnes, D.A., and Thorner, J. (1986) *Mol. Cell. Biol.*, vol. 6, pp. 2828–2838.
Rothstein, R.J. (1983) *Methods Enzymol.*, vol. 101, pp. 202–211.
Coleman, J. (1990) *J. Biol. Chem.*, vol. 265, pp. 17415–17221.
Kawaguchi, A., Yoshimura, T., and Okuda, S. (1981) *J. Biochem.*, vol. 89, pp. 337–339.
Steiner, M.R., and Lester, R.L. (1972) *Biochim. Biophys. Acta*, vol. 260, pp. 222–243.
Klein, P., Kanehisa, M., and DeLisi, C. (1985) *Biochim. Biophys. Acta*, vol. 815, pp. 468–476.
Eisenberg, D., Schwarz, E., Komaromy, M., and Wall, R. (1984) *J. Mol. Biol.*, vol. 179, pp. 125–142.
Rao, M.J.K., and Argos, P. (1986) *Biochim. Biophys. Acta*, vol. 869, pp. 197–214.
Pearson, W.R., and Lipman, D.J. (1988) *Proc. Natl. Acad. Sci. U.S.A.*, vol. 85, pp. 2444–2448.
Luttinger, A.L., Springer, A.L., and Schmid, M.B. (1991) *New Biologist*, vol. 3, pp. 687–697.
Olsen, M.V. et al., (1986) *Proc. Natl. Acad. Sci. U.S.A.*, vol. 83, pp. 7826–7830.
Mullen, J.R. et al., (1989) *EMBO J.*, vol. 8, pp. 2067–2075.
Schuller, H.J., Hahn, A., Troster, F., Schutz, A., and Schweizer, E. (1992) *EMBO J.*, vol. 11, pp. 107–114.
Nikoloff, D.M., and Henry, S.A. (1991) *annu. Rev. Genet.*, vol. 25, pp. 559–583.
Dorsman, J.C. et al., (1989) *Nucleic Acids Res.*, vol. 17, pp. 4917–4923.
Halfter, H., Muller, U., Winnacker, E.L., and Gallwitz, D. (1989) *EMBO J.*, vol. 8, pp. 3029–3037.
Dobrowsky, R.T., and Hannun, T.A. (1992) *J. Biol. Chem.*, vol. 267, pp. 5048–5051.
Dressler, K.A., Mathias, S., and Kolesnick, R.N. (1992) *Science*, vol. 255, pp. 1715–1718.
Patton, J.L., Srinivasan, B., Dickson, R.C., and Lester, R.L. (1992) *J. Bacteriol.*, vol. 174, pp. 7180–7184.
Higgins, D.G., and Sharp, P.M. (1988) *Gene (Amst.)*, vol. 73, pp. 237–244.

(List continued on next page.)

*Primary Examiner*—George C. Elliott
*Assistant Examiner*—Robert Schwartzman
*Attorney, Agent, or Firm*—Lowe, Price, LeBlanc & Becker

[57] ABSTRACT

A method for specifying a fatty acid at the sn2 position of acylglycerol lipids including (a) transfecting a vector including the SLC1 gene or a variant thereof into embryonic biological material, and (b) allowing the SLC1 gene to specify the type of fatty acid at the sn2 position of acylglycerol lipids. Also provided for is an isolated SLC1 gene and a probe for its detection.

10 Claims, 16 Drawing Sheets

OTHER PUBLICATIONS

Johnston, S.A., and Hopper, J.E. (1982) *Proc. Natl. Acad. Sci. U.S.A.*, vol. 79, pp. 6971–6975.

Chemical Abstracts, vol. 92, Abstract 17761w, (1980) "Characterization of sterol ester synthetase in *Saccharomyces cerevisiae*".

Chemical Abstracts, vol. 91, Abstract 1882621j, (1979) "Utilization of endogenous diacyl glycerol for the synthesis of tricylglycerol, phosphatidylcholine and phosphatidyl ethanolamine by lipid particles form baker's yeast".

Chemical Abstracts, vol. 88, Abstract 165910b, (1978), "Glycerolipid biosynthesis in *Saccharomyces cerevisiae*".

Chemical Abstracts, vol. 87, Abstract 129342p, (1977), "Acyltransferase systems involved in phospholipid metabolism in *Saccharomyces cerevisiae*".

Chemical Abstracts, vol. 105, Abstract 94333x, (1986), "Mutants of *Saccharomyces cerevisiae* defective in sn–glycerol–3–phosphate acyltransferase. Simultaneous loss of dihydroxy acetone phosphate acyltransferase indicates a common gene".

Chemical Abstracts, vol. 115, Abstract 274626k, (1991), "Acyl CoA–cholesterol acyltransferase (ACAT) inhibitors from microbial and plant lipids".

Chemical Abstracts, vol. 114, Abstract 38917q, (1991), "Genetic and biochemical studies of sn–glycerol–3–phosphate acyltransferase in *Saccharomyces cerevisiae*".

Chemical Abstracts, vol. 117, Abstract 167433q, (1992), "The acyl dihydroxyacetone phosphate pathway enzymes for glycerolipid biosynthesis are present in the yeast *Saccharomyces cerevisiae*".

Nagiec et al. J. Biol. Chem. 268:22156–22163, Oct. 15, 1993.

(SEQ ID NO:1)

(SEQ ID NO:2)

-1124 CTTCTTATTTTGGGGAATTTAGGCAAGTTTTTCTTCTTATGGCCGTTAAAGGATCTTGA
-1064 TCTACCGCTGAAGTTTTGGACTTCGAGGCCCTCGTGTAAATCAAACTGTTTTTTCGT
-1004 CAAAACACTCAGTTTCTTACCTTCATATGACAAATTCGTTGACTCATCGTCATTGGA
-944 ATACGATTTCAAAAAAGCTTCACATTCTGAATTGTCTTAAATTCCACCAAGACCGTACC
-884 ATTAAATTTCTTGTTTCTGATCTCTTCCAAACGCACTTGGTTGATTTCACCTAATTT
-824 TTTGAAAAAGGCTTCCAAGTTCTCCTGCAATTCTGAATTTGGGAAGCTTCAACGTCCTC
-764 ATGTGGGAAATTCATTACAGCCAAAGTCCGTTGGTTTGCTCAATTCTGGCATTCTGGC
-704 AGCAGTTAGTCCAAAGGAACACGTCTCTTGACGTTCTCTCCATCAGCAGATACTTCCAA
-644 AATTTCAGAACTACGTAGTGCTTCGATAAACCTTATCCACTGGTCTATATTCTTCATACG
-584 GTTGAATGTGGCGATGGTGCTGATGGGACCCATCCATCGTTTTTTCCGCTGTGTGCG
-524 CAAGAACCTGTCATATGGAAGTTGAATTGAAGTTAAATCAGAAAGTAGACAAATGAATTAACA
-464 TCTGTCCAAGACTTCTGGAGTAAATTCAATCACACGCAAATGAATTACGTCTTGATTGTGG
-404 TTTCTCTGCTCCTCTGTGTTTTGGTTTTGTCAGATGCTACTTTA
-344 GTTCCAGTAGAACCAAATAGAACCCATTTTTGAAAAAGAAATCTTGAGATATTGCGAT
-284 TGAGATGCGACTCGTGCTTGAACACATTGATGATATCAAAAATCTTGAGAATATGGTATG
-224 GAGGTTGGGCTGAACACATTGATGATATATTAGGAAGACGAATTCTTCAATAGAGA
-164 TGGATCTCGTGAATGATACTTATATATTAGGAAGGTTAAGGTGAAGGGAATTCTTCAATAGAGA
-104 GTGTTCAAAATACTTATATATTAGGAAGGTTAAGGTGAAGGGGAATTCTTCAATAGAGA
-44 AGTTTAGTGGTTTCCCTGCCCGTCAGTGAATTCGAGCAGTGAATAATGAGTGTGATAGGTA
                                                  M  S  V  I  G        5

17 GGTTCTTGTATTACTTGAGGTCCGTGTGGCCAGGCTGTGGGCTTTT
     R  F  L  Y  Y  L  R  S  V  L  V  V  L  A  L  A  G  C  G  F      25
77 ACGGGTGTAATCGCCTCTATCCTTTGCACGTTAATCGGTAAGCAACATTGGCTCAGTGGA
     Y  (G) V  I  A   S  I  L  C  T  L  I  G  K  Q  H  L  A  Q  W      45
137 TTACTGCGCGTTGTGTTTTTACCATGTCATGAAATTGATGCTTGGCCTTGACGTCAAGGTCG

FIG. 2A

```
        I   T   A   R   C   F   Y   H   V   M   K   L   M   L   G   L   D   V   K   V    65
197   TTGGCGAGGAGAATTTGGCCAAGAAGCCATATATTATGATTGCCAATCACCACCT
        V   G   E   E   N   L   A   K   K   P   Y   I   M   I   A   N   H   Q   S   T    85
257   TGGATATCTTCATGTTAGGTAGGATTTTCCCCCTGGTTGCACAGTTACTGCCAAGAAGT
        L   D   I   F   M   L   G   R   I   F   P   P  (G)  C   T   V   T   A   K   K   105
317   CTTTGAAATACGTCCCCTTTCTGGTTGGTTCATGGCTTTGAGTGGTACATATTTCTTAG
        S   L   K   Y   V   P   F   L   G   W   F   M   A   L   S   G   T   Y   F   L   125
377   ACAGATCTAAAAGGCAAGAAGCCATTGACACCTTGAATAAAGGTTTAGAAAATGTTAAGA
        D   R   S   K   R   Q   E   A   I   D   T   L   N   K   G   L   E   N   V   K   145
437   AAAACAAGCGTGCTCTATGGGTTTTTCCTGAGGGTACCAGTCTTACACGAGTGAGCTGA
        K   N   K   R   A   L   W   V   F   P   E   G   T   R   S   Y   T   S   E   L   165
497   CAATGTTGCCTTTCAAGAAGGGTGCTTTCCATTGGCACAACAGGGTAAGATCCCCATTG
        T   M   L   P   F   K   K   G   A   F   H   L   A   Q   Q   G   K   I   P   I   185
557   TTCCAGTGGTTGTTGTTTCCAATACCAGTACTTTAGTAAGTCCTAAATATGGGTCTTCAACA
        V   P   V   V   S  [N]  T   S   L   V   S   P   K   Y   G   V   F   N   205
617   GAGGCTGTATGATTGTTAGAATTTAAAACCTATTTCAACCGAGAACTTAACAAAGGACA
        R   G   C   M   I   V   R   I   L   K   P   I   S   T   E  [N]  L   T   K   D   225
677   AAATTGGTGAATTTGCTGAAAAAGTTAGAGATCAAATGGTTGACACTTTGAAGGAGATTG
        K   I   G   E   F   A   E   K   V   R   D   Q   M   V   D   T   L   K   E   I   245
737   GCTACTCTCCCGCCATCAACGATACAACCCTCCCACCACAAGCTATTGAGTATGCCGCTC
        G   Y   S   P   A  [N]  D   T   T   L   P   P   Q   A   I   E   Y   A   A   265
797   TTCAACATGACAAGATGTCAATACCCATAACGAAAATCAAGAATGAGCCTGTGCCTTCTGTCAGCA
        L   Q   H   D   K   K   V   N   K   K   I   K   N   E   P   V   P   S   V   S   285
857   TTAGCAACGATGTCAATACCCATAACGAAGGTTCATCTGTAAAAAAGATGCATTAAGCCA
        I   S   N   D   V   N   T   H   N   E   G   S   S   V   K   K   M   H   -    303
```

FIG. 2B

```
 917 CCACCACATTTTTAGAGTAGTAGTATATAGACCCAAAAACTGTAATTATCTTTTAAAAAGT
 977 AAAATGACTTACGAATGATTCTGATGATTTTATTTATTACGACTCATATACCCAGCGTAA
1037 GAAGTGATCAATAGACCGCTACTTTATTCGGAGAAAGAGAAAAGAACTTTCCATTGTAAT
1097 GTATATATAACACCAGGCATGTGTCAAAAATGTGAGACTAAATAGAAAGAAAAATACGAG
1157 GAACAACAAATAATACGATCTTGTGCATATTTTTCCCTTTTTTTTTTAATTCTTTTTT
1217 TCTGAAATTTTCATTTGTTCACTGTTTAATATCTATCCATTTTGTTTCCGAATTTTCA
1277 TTAACTTTATTACTTATTTACGATACAATTTCCCTTAATCTAGTACGAAATGACAACA
1337 ACCTCAACAACCAGTGTAGATGGCAGAACCTCCTCGACTTTGAAGGCTACTTTATCTGCT
1397 TCAGGTCCAAATTCAAATGGTCCAAGCCCCGCTGTGCTTCCTCAGAAGCCAAAATTAACA
1457 GGTTGGGCGCAGGCAGCTGCCAAAGCCCCTCCAAGGCAACAGCAACAGCAACAGCAGGCA
1517 CGAAAAGATGATTCCGTGGCTGTACAACCTGCTAATACGAAGACTAAAACCATCGCATCT
1577 ACCGCGCCGCCTGCTAATATAAAGGGTAGTTCCACCGCCAATGATCATCCACAAATAAG
1637 AAATTTAAAGAGCGAATAACCTTACAATAGAACCTTGGTGAAAAAGTCATTCAATGAAAACTTATAAGCAA
1697 AAATTATTTCAGAAAACGGCAAGTGGCAGAGTTTCAACAGCCACTGACTGGGTACTGTATCA
1757 GTACTATCAGAAACGGCAAGTGGCAAGAATAAAAATACGGCTGTTTGTCCGATATTGCTAAAGTTTTAAGA
1817 AGCAGTAAAAATAAGAATATCGAAGCATCACGTTTCATAACGCAAAAAGGAGTCAAACAAAAAT
1877 AACCAATGAGAATATCGAAGCATCACGTTTCATAACGCAAAAAGGAGTCAAACAAAAAT
1937 GAAGTATGAAGTCAAGATAAAACGAAGAAAAGAGAAAATAGAAGAAATGAAAATATTATTT
1997 TACAAGCGTAAATAAAAATTTTATAATTCATAATGTCGAAAAATGTATACTGTGTTAAGA
2057 CGCCTTTCTTTGCTTTTTCTCTTAGTCTTTTATTGCATAGTTCACTTAGCCTTTCCGATGC
2117 TAGC
```

FIG. 2C

```
SLC1  MSVIGRFLYYLRSVL-VVLALAGCGFYGVIASILCTLIGKQHLAQWITAR    49  (SEQ ID NO:2)
PLSC  M------LYIFRLIITVIYSILVCVF----GSIYC-LFSPRNPKHVATFG    39  (SEQ ID NO:3)
PARF  M------LYIFRLIVTVIYSILVCVF----GSIYC-LFSPRNPKHVATFG    39  (SEQ ID NO:4)
            *      .** . ...* .    ****  *

SLC1  CFYHVMKLMLGLDV---KVVGEENLAKKPYIMIANHQSTLDIFMLGRIFP    96
PLSC  HMFGRLAPLFGLKVECRKPTDAESYGNAIYI--ANHQNNYDMVTASNIVQ    87
PARF  HMFGRLAPLFGLKVECRKPADAENYGNAIYI--ANHQNNYDMVTAANIVQ    87
       .* .  *  **   .  *. ** ***      ***.  *  *.  *

SLC1  PGCTVTAKKSLKYVPFLGWFMALSGTYFLDRSKRQEAIDTLNKGLENVKK   146
PLSC  PPTVTVGKKSLLWIPFFGQLYWLTGNLLIDRNNRTKAHGTIAEVVNHFKK   137
PARF  PPTVTVGKKSLLWIPFFGQLYWLTGNLLIDRNNRAKAHSTIAAVVNHFKK   137
      * .**  ****  .**  *  * ..   ****.    .*  * *. .**

SLC1  NKRALWVFPEGTRSYTSELTMLPFKKGAFHLAQQGKIPIVPVVVSNTSTL   196
PLSC  RRISIWMFPEGTRSRGRGL--LPFKTGAFHAAIAAGVPIIPVCVSTTSNK   185
PARF  RRISIWMFPEGTRSRGRGL--LPFKTGAFHAAIAAGVPIIPVCVSNTSNK   185
       ..  *.*******       *** ****      .**.**.**.**.

FIG. 3A
```

```
SLC1  VSPKYGVFNRGCMIVRILKPISTENLTKDKIGEFAEKVRDQMVDTLKEIG  246
PLSC  IN--LNRLHNGLVIVEMLPPIDVSQYGKDQVRELAAHCRSIMEQKIAELD  233
PARF  VN--LNRLNNGLVIVEMLPPVDVSEYGKDQVRELAAHCRALMEQKIAELD  233
        .  .  . .* .*** . **   .     .   **. *  .  *  .

SLC1  YSPAINDTTLPPQAIEYAALQHDKKVNKKIKNEPVPSVSISNDVNTHNEG  296
PLSC  ------------------------------------------KEVAEREAA  242
PARF  ------------------------------------------KEVAEREAT  242
                                                  . .*

SLC1  SSVKKMH  303
PLSC  GKV----  245
PARF  GKV----  245
      ..*
```

FIG. 3B

```
                    T  Y  T  T  C  C  A  C  A  T  G  Y
SLC1 pos.-503/-513: T  T  T  T  C  C  A  T  A  T  G  A    (SEQ ID NO:5)
SLC1 pos.-746/-756: T  T  T  C  C  C  A  C  A  T  G  A    (SEQ ID NO:6)

CONSENSUS ICRE:     T  Y  T  T  C  C  A  C  A  T  G  Y    (SEQ ID NO:7)

TECHNIQUE FOR SPECIFYING THE FATTY ACID AT THE SN2 POSITION OF ACYLGLYCEROL LIPIDS

TECHNICAL FIELD

The present invention is directed to a technique for specifying the fatty acid at the sn2 position of acylglycerol lipids in biological material. Also provided is an isolated SLC1 gene and a probe for its detection.

BACKGROUND

All membranes of living cells contain glycerophospholipids which have fatty acid attached to the 1 and 2 carbons of the 3-carbon glycerol molecule. The fatty acids at these two positions have different numbers of carbon atoms and degrees of unsaturation (a double bond between the two carbon atoms). The length of the fatty acid and degree of saturation have important dietary consequences for man. For example, diets rich in saturated fatty acids are associated with increased risk of coronary artery disease whereas monounsaturated fatty acids are associated with decreased risk. Plant seed also consist largely of triacylglycerol-glycerol having three fatty acids.

The type of fatty acids present in glycerolipids is determined by enzymes called fatty acyltransferases. The present inventors isolate the first eucaryotic gene, SLC1 that encodes a transferase specific for the 2 position of glycerolipids from *Saccharomyces cerevisiae*.

Determining the biological function(s) and mode of action of individual sphingolipids in multicellular eucaryotes has proven to be a challenging and unfinished task because of the great variety of sphingolipids present in such organisms (1–3, see reference citations below). In contrast to this variety, the unicellular eucaryote *Saccharomyces cerevisiae* has only one major and two minor types of structurally related sphingolipids. Such simplicity provides a unique opportunity to study sphingolipid function(s) in an organism to which molecular genetic techniques can be readily applied.

The most abundant sphingolipid in *S. cerevisiae* is mannosyldiinositolphosphorylceramide with lesser amounts of inositolphosphorylceramide and mannosylinositolphosphorylceramide (4,5). The ceramide moiety contains the sphingoid long chain base phytosphingosine linked by an amide bond to a $C_{26}$ fatty acid (4).

Synthesis of phytosphingosine initiates with the condensation of serine and palmitoyl-CoA catalyzed by serine palmitoyltransferase to yield 3-ketodihydrosphingosine (6). In *S. cerevisiae* the enzyme or one of its subunits is encoded by the LCB1 gene (7). Strains defective in lcb1 lack serine palmitoyltransferase activity and have an Lcb⁻ phenotype because they require a long chain base such as phytosphingosine for growth (8–10). The Lcb⁻ phenotype provides a starting point for a molecular genetic analysis of sphingolipid function(s). *Saccharomyces cerevisiae* normally requires sphingolipid biosynthesis for growth.

Some glycerolipids of *Saccharomyces cerevisiae* are known. For example, U.S. Pat. No. 5,057,419 is entitled Genetically Engineered Plasmid and Organisms for the production of Specialized Oils. This patent discloses an expression vector encoding a yeast delta-9 fatty acid desaturase enzyme which functions in a yeast cell to induce or enhance oil production. The overproduction of delta-9 desaturase by the cells leads to the production of abnormally high levels of unsaturated fatty acids in the cell membrane. In order to compensate for the increased levels of unsaturated fatty acids in the lipids, excess unsaturated fatty acids are removed from the membrane lipids and shunted into triglyceride formation. The yeast are indicated to overproduce oils containing polyunsaturated fatty acid with superior properties.

U.S. Pat. No. 5,288,619 to Moore discloses a process for industrial enzymatic interesterification of a triglyceride including steps of reacting a triglyceride in an enzyme conversion zone. The enzymes which are used are preferably 1,3 specific lipases.

U.S. Pat. No. 5,286,633 to Brown et al. discloses an enzymatic transesterification method for preparing a margarine oil. The margarine oil product has a non-random fatty acid distribution in which esterified stearic acid is predominantly distributed in the 1,3-positions while esterified unsaturated fatty acid moieties are in higher concentration in the 2- position of the glycerides. The method of making the margarine oil includes a step of providing a transesterification reaction mixture comprising stearic acid and triglyceride vegetable oil and transesterifying using a 1,3 lipase. Enzymes from synthetic sources are contemplated, including yeasts.

Chemical Abstracts, Vol. 92, Abstract 17761w, (1980) "Characterization of sterol ester synthetase in *Saccharomyces cerevisiae*" discloses that cell free extracts of *Saccharomyces cerevisiae* catalyzed the synthesis of fatty acid ester of sterol from cholesterol, fatty acid, ATP, and CoA or from cholesterol and fatty acyl CoA. The enzyme involved in the formation of the ester is acyl-CoA-sterol-O-acyltransferase.

Chemical Abstracts, Vol. 91, Abstract 188621j, (1979) "Utilization of endogenous diacyl glycerol for the synthesis of triacylglycerol, phosphatidylcholine and phosphatidyl ethanolamine by lipid particles from baker's yeast" discloses a measurement of the activity of 3 enzymes prepared from *S. cerevisiae* in the presence of 1,2-diacylglycerol substrates. The enzymes include diacylglycerol acyltransferase, choline phosphotransferase, and ethanolamine phosphotransferase.

Chemical Abstracts, Vol. 88, Abstract 165910b, (1978), "Glycerolipid biosynthesis in *Saccharomyces Cerevisiae*" discloses an investigation of *S. cerevisiae* dihydroxyacetone phosphate acyltransferase to determine whether its activity and that of glycerol phosphate acyltransferase represent dual catalytic functions of a single membranous enzyme.

Chemical Abstracts, Vol. 87, Abstract 129342p, (1977), "Acyltransferase systems involved in phospholipid metabolism in *Saccharomyces cerevisiae*" discloses membrane preparations of *S. cerevisiae* catalyzed the acylation of glycerophosphate, 1 acyl- and 2 acyl-glycerophosphates and 1 acyl- and 2 acyl-glycerylphosphocholines. Specificity of glycerophosphate acyltransferase, 2-acylglycerophosphate acyltransferase and 1-acylglycerophosphate acyltransferase were determined.

Chemical Abstracts, Vol. 105, Abstract 94333x, (1986), "Mutants of *Saccharomyces cerevisiae* defective in sn-glycerol-3-phosphate acyltransferase: Simultaneous loss of dihydroxy acetone phosphate acyltransferase indicates a common gene" discloses the isolation of fourteen independent mutants defective in sn-glycerol-3-phosphate acyltransferase activity.

Chemical Abstracts, Vol. 115, Abstract 274626k, (1991), "Acyl CoA-cholesterol acyltransferase (ACAT) inhibitors from microbial and plant lipids" discloses that enzyme ACAT, responsible for absorption of cholesterol by the intestinal epithelium is inhibited by fatty acid-like substances obtained from enzymatic degradation products of microbial and plant products.

Chemical Abstracts, Vol. 114, Abstract 38917q, (1991), is directed to "Genetic and biochemical studies of sn-glycerol-3-phosphate acyltransferase in *Saccharomyces cerevisiae*". Chemical Abstracts, Vol. 117, Abstract 167433q, (1992), "The acyl dihydroxyacetone phosphate pathway enzymes for glycerolipid biosynthesis are present in the yeast *Saccharomyces cerevisiae*" discloses studies of the acyl dihydroxyacetone phosphate pathway enzymes for glycerolipid biosynthesis. This pathway is used in yeast *Saccharomyces cerevisiae* non-ether glycerolipid synthesis.

There is a need in the art for a knowledge of the SLC1 gene of *Saccharomyces cerevisiae* and its use to construct economically and dietetically important plants, such as seeds, from which cooking oils are obtained which have fatty acids with optimal benefits, as well as better storage properties. Likewise, there is a need to produce animals whose meat products would contain glycerolipids with fatty acids having different degrees of saturation and/or chain length. Such changes improve the flavor and storage properties and reduce adverse effects on humans, for example, by reducing the percentage of polyunsaturated fatty acids. The present invention provides these benefits and overcomes the deficiencies and lack of knowledge of the prior art.

DISCLOSURE OF THE INVENTION

An object of the present invention is to provide a technique for specifying the fatty acid at the sn2 position of acylglycerol lipids.

The method for specifying a fatty acid at the sn2 position of acylglycerol lipids includes (a) transfecting a vector including the SLC1 gene or a variant thereof into embryonic biological material, and (b) allowing the SLC1 gene to replicate to direct fatty acid at the sn2 position of acylglycerol lipids. The biological material may be plant or animal embryonic material.

The invention provides for isolation and characterization of the SLC1 gene of *Saccharomyces cerevisiae*. Also provided for is an isolated SLC1 gene and a probe for its detection.

In an alternative embodiment, the invention provides for use of the SLC1 gene of *Saccharomyces cerevisiae* as a probe for isolation of homologous gene sequences in other organisms. The probe may be labeled by methods known in the art.

The invention provides for use of the SLC1 gene to construct economically and dietetically important plants, such as seeds from which cooking oils are obtained which have fatty acids with optimal benefits, as well as better storage properties. Likewise, there is a need to produce animals whose meat products would contain glycerolipids with fatty acids having different degrees of saturation and/or chain length. Such changes improve the flavor and storage properties and reduce adverse effects on humans, for example, by reducing the percentage of polyunsaturated fatty acids.

BRIEF DESCRIPTION OF DRAWINGS

FIG. 2 shows the nucleotide sequence of SLC1. Shown below the SLC1 nucleotide sequence (SEQ ID NO:1) is the protein sequence. A membrane spanning domain is underlined. N-linked glycosylation sites are indicated by brackets, and putative N-myristoylation sites are indicated by parentheses. A start codon for ORFX is indicated by the CAT sequence upstream of the SLC1 start codon. Putative inositol/choline response elements upstream of the SLC1 start codon are double underlined. Nucleotide 131 is mutated from an A to a T in the SLC1-1 suppressor allele (shown in bold).

FIG. 3 shows protein homology. The SLC1 protein sequence (SEQ ID NO: 2) was aligned with the *E. coli* PlsC protein (PLSC) (SEQ ID NO:3) and the *S. typhimurium* parF protein (PARF) (SEQ IS NO:4) using the program CLUSTAL (39). Amino acid residues identical in the three proteins are indicated by an asterisk below the sequence; similar residues are indicated by a dot.

FIG. 10 shows putative promoter elements (SEQ ID NO:5–7). Inositol/choline response elements (ICRE) identified by computer analysis of the SLC1 promoter and their location upstream of the ATG start codon are indicated at the top of the figure. The data (32) from which the consensus sequence was derived are indicated at the bottom of the figure.

DESCRIPTION OF THE INVENTION

Figure 1:
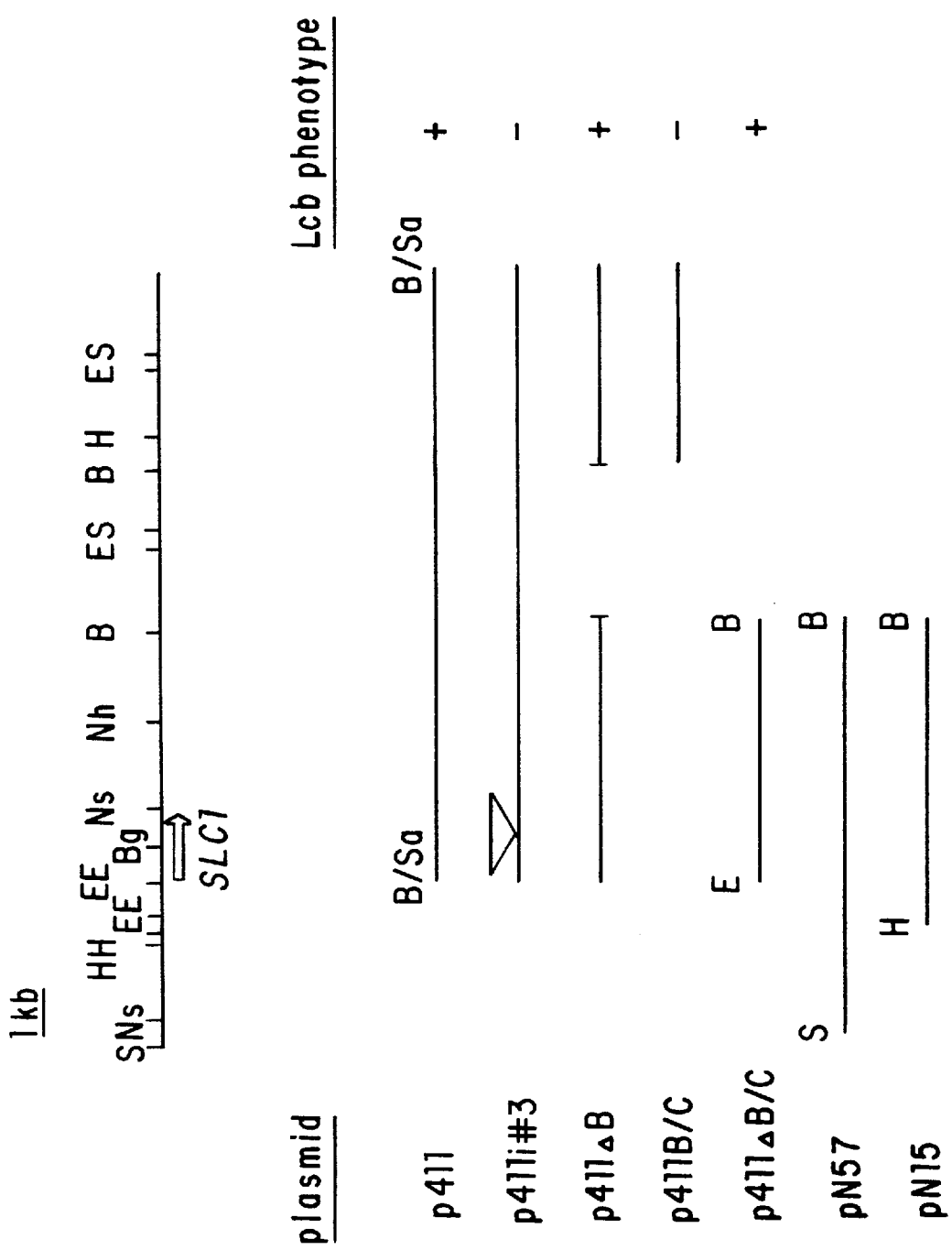
FIG. 1 shows a restriction map of the SLC1 chromosomal locus and plasmid subclones. The location of the SLC1 open reading frame is denoted by the open arrow. p411 is plasmid YEp434 carrying an 8.5-kb DNA fragment that contains the SLC1-1 suppressor allele. Only the insert portion of each plasmid is shown. Derivatives of p411 carrying a portion of the original insert are shown as is 411i#3, which carries an unspecified 500-bp Sau3A1 fragment obtained from YEp434 and inserted into the BglII site of p411. The ability of plasmids to confer an Lcb$^+$ phenotype on Lcb$^-$ strain 1Δ4 is indicated. pN57 and pN15 are integrating vectors carrying the SLC1 gene retrieved from strain 1Δ4 using pRS305. Restriction endonuclease sites are: B, BamHI; B-Sa, BamHI-Sau3A1 junction; Bg, BglII; E, EcoRI; H, HindIII; Nh, NheI; Ns, NsiI; S, SalI.

Saccharomyces cerevisiae normally requires sphingolipid biosynthesis for growth. However, mutant strains lacking sphingolipids have been isolated by suppression of a genetic defect in sphingolipid long chain base biosynthesis.

To begin to understand the nature of the suppressor(s), a suppressor gene, SLC1 (sphingolipid compensation) was isolated and characterized. DNA sequence analysis showed that the wild type SLC1 allele differs from the suppressor allele by a single nucleotide which changes Gln-44 in the predicted wild type protein to Leu-44 in the predicted SLC-1 suppressor protein. The SLC1 protein sequence is homologous to the 1-acyl-sn-glycerol-3-phosphate acyltransferase of Escherichia coli encoded by the plsC gene. The homology extends to function as well since the SLC1 gene complements the growth defect in an E. coli strain mutated in plsC. These results suggest that the SLC1 protein has a fatty acyltransferase activity. SLC1 thus is the first eucaryotic sn2-acylglyceride fatty acyltransferase gene to be cloned.

SLC (sphingolipid compensation) strains grown in the absence of long chain base make novel phosphatidylinositol derivatives (Lester, R. L., Wells, G. B., Oxford, G., and Dickson, R. C. (1993) J. Biol. Chem. 268, 845–856) having a C26 fatty acid at the sn-2 position and the same polar head groups as normal sphingolipids. The SLC1 suppressor allele encodes a variant enzyme with an altered substrate specificity that enables it to use a $C_{26}$ in place of a $C_{16/18}$ fatty acid precursor to acylate the sn-2 position of inositol-containing glycerolipids.

The most abundant sphingolipid in S. cerevisiae is mannosyldiinositolphosphorylceramide with lesser amounts of inositolphosphorylceramide and mannosylinositolphosphorylceramide (4,5). The ceramide moiety contains the sphingoid long chain base phytosphingosine linked by an amide bond to a $C_{26}$ fatty acid (4).

Synthesis of phytosphingosine initiates with the condensation of serine and palmitoyl-CoA catalyzed by serine palmitoyltransferase to yield 3-ketodihydrosphingosine (6). In S. cerevisiae the enzyme or one of its subunits is encoded by the LCB1 gene (7). Strains defective in lcb1 lack serine palmitoyl-transferase activity and have an Lcb⁻ phenotype because they require a long chain base such as phytosphingosine for growth (8–10). The Lcb⁻ phenotype provides a starting point for a molecular genetic analysis of sphingolipid function(s).

A second site suppressor mutation, SLC1-1, in the yeast genome relieves the need for making phytosphingosine, and hence sphingolipids, and thus allows an lcb1 deletion mutant to grow in the absence of exogenous phytosphingosine.

To confirm this, mutant strains, SLC (sphingolipid compensation), were shown to grow without making detectable sphingolipids (11) because of a mutation in a suppressor gene termed SLC1.

The next step in understanding the function of sphingolipids was to determine the biochemical effects of the SLC1 gene. The inventors show that when lcb1-defective cells carrying the SLC1 suppressor gene are grown in the absence of phytosphingosine they make a set of novel lipids (12) which contain the same polar head groups and the $C_{26}$ fatty acid moiety found in yeast sphingolipids. Instead of ceramide, however, the lipid moiety consists of diacylglycerol esterified with one $C_{26}$ fatty acid at the sn-2 position and one medium chain fatty acid at the sn-1 position. These lipids may allow cell growth by acting as partial functional analogs of sphingolipids.

The isolation and characterization of the SLC1-1 suppressor gene is described. A single amino acid change in the SLC1-1 protein is responsible for suppression of the Lcb⁻ phenotype and production of the suppressor lipids.

Figure 11:
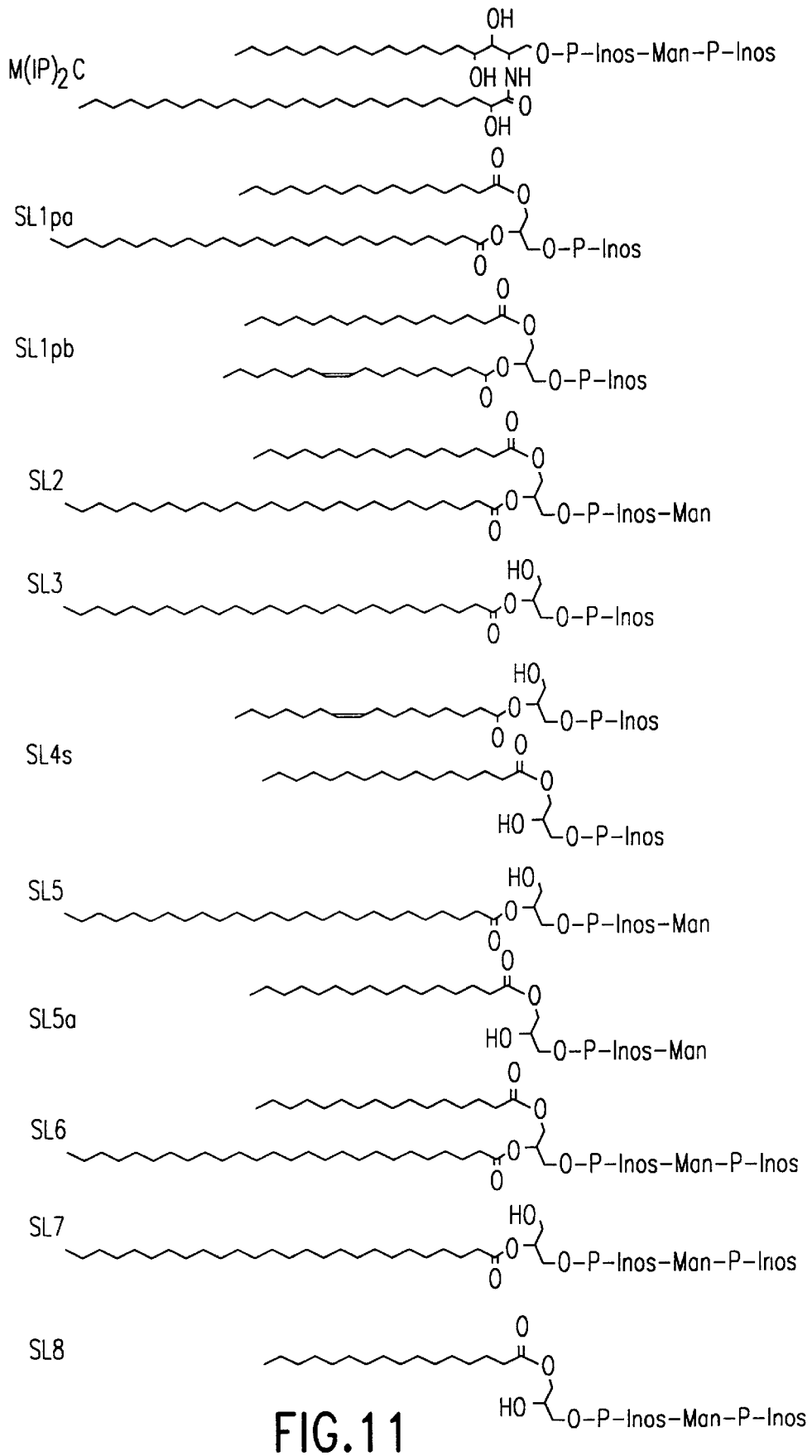
FIG. 11 shows that when SLC cells grown in the absence of phytosphingosine make the novel suppressor lipids (depicted in the figure) and the cells have altered phenotypes.

A direct application of this invention is that properties such as phenotypes of unicellular and multicellular plant or animal organisms can be changed by altering the fatty acid at the sn-2 position of glycerolipids. In support of this embodiment it has been demonstrated previously (Patton et al., 1992) that when SLC cells are grown in the absence of phytosphingosine, that is when they make the novel suppressor lipids (shown in 12, FIG. 9; see also FIG. 11 above), the cells have altered phenotypes. For example, they do not grow at 37° C., at a pH of 3.5, or in the presence of 0.75 M NaCl or KCl. Their inability to grow at low pH is related to the fact that they are more permeable to protons or have a reduced ability to pump protons out of the cell (FIG. 2, Patton et al., 1992).

Experimental Procedures

Strains - The yeast strains used are described in Table I. Yeast were grown on rich (PYED) or minimal (SD) medium supplemented, when necessary, with 25 μM phytosphingosine as described previously (7). *Escherichia coli* strains JC200 (thr-1 ara-14 Δ(gal-attλ)-99 hisG4 rspL136 xyl-5 mtl-1 lacY1 tsx-78 eda-50 rfbD1 thi-1 (13) and JC201, a derivative of JC200 carrying a temperature-sensitive mutation in plsC which prevents growth at temperatures above 42° C., were used as described.

TABLE I

Yeast Strains

| Strain | Genotype | Ref. |
|---|---|---|
| SJ21R | leu2-3, 112, ade1, MEL1 | 40 |
| 1Δ4 | leu2-3, 112, ade1, MEL1, lcb1::URA3 | 11 |
| 4R3 | leu2-3, 112, ade1, MEL1, lcb1::URA3,SLC1-1 | This Study |
| 4R3-1 | strain 4R3 with slc1Δ2::LEU2 | This Study |
| 7R6 | leu2-3, 112, ade1, MEL1, lcb1::URA3,SLC1-1 | 11 |
| 7R4 | leu2-3, 112, ade1, MEL1, lcb1::URA3,SLC2-1 | 11 |
| BS238 | leu2-3, 112, ade1, MEL1, lcb2 | 9 |
| YPH2 | lys2-801, ade2-101 | 17 |

Recombinant DNA Library Construction and DNA Manipulations - Genomic DNA, isolated (14) from strain 4R3, was partially digested with restriction enzyme Sau3A1 and separated on 0.8% agarose gel (Sea Plaque, FMC BioProducts, Rockland, Me.). DNA fragments of 5–15 kb$^1$ were isolated from the gel and ligated to the yeast multicopy vector YEp434 (15) which had been linearized by digestion with BamHI and treated with alkaline phosphatase. Ligated DNA was transformed into $CaCl_2$-treated *E. coli*. *E. coli* transformants (27,000) were pooled, and plasmid DNA was purified. More than 90% of the plasmids had an insert with an average size of 8 kb.

DNA Sequencing - Most of both strands of the 3.5-kb EcoRI-BamHI DNA fragment carried in plasmid p411ΔB/C (see FIG. 1) were sequenced using the dideoxynucleotide procedure and Sequenase 2.0 (U.S. Biochemical Corp.) as described in the Sequenase 2.0 kit. The GenBank accession number of SLC1 is L13282.

Cloning SLC1 Alleles - The wild type SLC1 allele, SLC1$^+$, was recovered from *S. cerevisiae* strain 1Δ4 by targeted site-specific plasmid integration and marker rescue (16). The 3.5-kb EcoRI-BamHI fragment carried in p411ΔB/C (FIG. 1) was recloned into the integrating vector pRS305 (17) to yield pRS305/411. Plasmid pRS305/411 was linearized by digestion with the restriction endonuclease NsiI, and linear plasmid DNA was transformed into strain 1Δ4. Leu+ transformants were selected, genomic DNA was isolated from several colonies and digested with SalI or HindIII, ligated, and transformed into *E. coli* with selection for ampicillin-resistant transformants. These operations gave pN57 (FIG. 1) from genomic DNA cleaved with SalI and pN15 (FIG. 1) from genomic DNA cleaved with HindIII. The 4.15-kb HindIII-BamHI fragment from pN15 was recloned into yeast CEN vector pRS315 (17) giving pRS315-WT which was used for transformation of strain 1Δ4. An identical approach was used to isolate the SLC1 locus from other suppressor strains.

Site-directed Mutagenesis - The A at position 131 of the SLC1$^+$ allele was changed to a T by site-directed mutagenesis exactly as described in the Muta-Gene kit (Bio-Rad) using a synthetic primer:

(5'-AGTAATCCACAGAGCCAAATG-3'(SEQ ID NO:8)).

M13 phage with the mutated DNA sequence were identified by restriction analysis. Mutant alleles yield a 527-bp DdeI restriction fragment instead of the two smaller fragments, 328 and 244bp, present in the wild type. A 2.9-kb HindIII-BamHI fragment from two mutant phages was recloned into vector pRS315, and the resulting plasmids, pRSM5 and pRSM9, were shown to confer an Lcb$^+$ phenotype on strain 1Δ4.

Northern Blot Hybridization - Total RNA was isolated from yeast strain SJ21R (18), and Northern blots were prepared exactly as described previously (19).

Riboprobes were synthesized using a Stratagene (La Jolla, Calif.) RNA transcription kit and [α-$^{32}$P]CTP (650 Ci/mmol; ICN Biomedicals Inc., Irvine, Calif.). The template for the LYS2 riboprobe was pBluescriptSK/LYS2, which carries LYS2 on a 4.6-kb EcoRI-HindIII fragment obtained from YEp620 (20). The template was digested with BamHI prior to RNA synthesis using T7 RNA polymerase so that a 1.4-kb runoff product complementary to the 3' end of the LYS2 mRNA was produced. The template for riboprobes T7E-N and T3E-N was plasmid PRSE-N. It has the 886-bp EcoRI-NsiI fragment from p411 cloned between the EcoRI and PstI sites of pRS305. The plasmid was cleaved with EcoRI and transcribed with T7 RNA polymerase to give riboprobe T7E-N, or it was cleaved with BamHI and transcribed with T3RNA polymerase to give riboprobe T3E-N.

The riboprobe T3A-N was made using T3 RNA polymerase and template pRS315WTΔHA digested with NsiI. pRS315WTΔHA was constructed by deleting a 967-bp HindIII-AatI fragment from pRS315-WT. Riboprobe T7H-RV was obtained by transcribing HindIII-digested pHRV with T7 RNA polymerase. This plasmid carries a 635-bp HindIII-EcoRV fragment from the insert of pN15 cloned between the HindIII and SmaI sites of pBluescriptKS (Stratagene). Riboprobe T3E-H was obtained by transcribing EcoRI-digested pRS315-WT with T3 RNA polymerase.

Chromosomal Replacement of SLC1- Deletion alleles of SLC1 were introduced into the yeast genome by the one-step gene disruption method (21). Deletion allele slc1Δ1::URA3 was constructed by replacing the 529-bp BglII-NsiI fragment in plasmid pRS305/411 with the 1-kb URA3 gene obtained as a BamHI-PstI restriction fragment. Plasmid pRS305/411 has the 3.4-kb EcoRI-BamHI fragment from p411, carrying the SLC1-1 suppressor allele, inserted into pRS305.

The resulting plasmid, pRS/411/URA3, was digested with EcoRI and BamHI and used to transform a diploid yeast strain (SJ21R/YPH2). The deletion allele slc1Δ2::LEU2 was constructed in two steps. First, the 529-bp BglII-NsiI fragment of pN15 was replaced with a 2.5-kb BamHI-SalI fragment, which carries LEU2, to yield pN15ΔBN::LEU2. Second, the 967-bp HindIII-AatI fragment of the pN15ΔBN::LEU2 was replaced with the same fragment from suppressor allele SLC1-1. The resulting plasmid, pSUΔN::LEU2, was digested with HindIII and BamHI and used for yeast transformation. Southern blot analysis confirmed the chromosomal structure of altered slc1 locus.

Assay of 1-Acyl-sn-glycerol-3-phosphate Acyltransferase - *E. coli* were grown at 30° C. on LB medium containing 0.1 mg/ml ampicillin for strains transformed with a plasmid. Homogenates and membranes were prepared as described (22) except that cell breakage was done with glass beads in a Braun homogenizer. The enzyme assay was performed at 30° C. as described previously (22) except that [$^3$H]oleyl-CoA (2.1×10$^6$ cpm/μmol) prepared according to (23) was the labeled precursor instead of glycerophosphate; incubation time, 20 min.

The lipids were extracted from the reaction mixture (24) and separated on SG-81 paper (Whatman) with the phospholipid solvent ($R_f$=0.6, phosphatidic acid) chloroform:methanol:acetic acid:water (32/4/5/1) and the neutral lipid solvent ($R_f$=0.37, diacylglycerol) benzene:chloroform:acetic acid (85/15/1).

Isolation and Characterization of a Suppressor Strain - These studies began with S. cerevisiae strain 1Δ4 which has the lcb1 gene deleted. The strain is phenotypically Lcb$^-$ because it requires a sphingolipid long chain base in the culture medium for growth (12). To obtain a derivative of strain 1Δ4 which suppressed the need for long chain base, cells were plated on PYED plates lacking the sphingolipid long chain base phytosphingosine and selected for Lcb$^+$ colonies, one of which, 4R3, was characterized in greater detail. This selection procedure is identical to one used previously to isolate suppressor strains 7R4 and 7R6 (ref.12 below, incorporated herein by reference in its entirety). Even though the suppressor mutation in strain 4R3 allows growth in media lacking long chain base, the suppressor does not restore a normal growth rate. On PYED medium lacking phytosphingosine the doubling time of 4R3 is about 4 h, whereas the doubling time is reduced to about 80 min (the same time as wild type cells) by the addition of 25 μM phytosphingosine to the medium. Also, without phytosphingosine in the culture medium, daughter cells tend to remain together and form large aggregates.

To determine if the suppressor mutation enables strain 4R3 to grow without making sphingolipids, the strain was grown in PYED medium lacking phytosphingosine, and cells were analyzed for their total phytosphingosine content. The data (Table II) demonstrate that strain 4R3 makes little if any free or bound phytosphingosine under these growth conditions; the value shown in Table II is at the limit of detection, and the actual value may be much lower. The strain is, however, capable of making the normal species and levels of sphingolipids if phytosphingosine is added to the culture medium (12), so the suppressor mutation does not interfere with normal sphingolipid synthesis.

TABLE II

Sphingolipid long chain base analysis of yeast strains
Long chain base content is expressed as pmol/absorbance unit at 650 nm (5 × 10$^{-6}$ cells). Analyses were done by methanolic-HCl hydrolysis of cells, extraction of the long chain base fraction, and conversion to UV-absorbing biphenylcarbonyl derivatives that were quantified after separation by reversed phase chromatography (12). The value for strain 4R3 is the mean and standard deviation for two separately grown cultures; the other values are for a single culture.

| Strain | $C_{18}$ + $C_{20}$ phytosphingosine pmol |
|---|---|
| SJ21R | 573 |
| 4R3 | 4 ± 2 |
| 1Δ4/p411 | 8 |
| 1Δ4/p411 | 5 |

Isolation of the Suppressor Gene - The suppressor gene from strain 4R3 was isolated from a genomic DNA library by transforming the library into the lcb1 deletion strain 1Δ4 (Lcb$^-$) with selection for Leu$^+$ transformants. About 12,000 Leu$^+$ cells were pooled and replated on PYED plates to select for Lcb$^+$ transformants that could survive without long chain base in the culture medium. Plasmid DNA from several Lcb$^+$ yeast colonies was rescued by transformation into E. coli and then shown to confer a Lcb$^+$ phenotype when retransformed into strain 1Δ4.

Several independent plasmid isolates were analyzed by restriction mapping and they appeared to carry the same 8.5-kb yeast DNA insert (p411, FIG. 1). The suppressor gene, SLC1-1, was localized as shown in FIG. 1 by testing subcloned regions of the insert DNA for their ability to suppress the Lcb$^-$ phenotype of strain 1Δ4.

Strain 1Δ4 Transformed with p411 Makes No Phytosphingosine - To confirm that the SLC1-1 gene suppresses the need for sphingolipids, the Lcb$^-$ strain 1Δ4 (relevant genotype lcb1::URA3) transformed with p411 was shown to make only a very low and barely detectable level of free or bound long chain base (Table II), about 100-fold below the level found in the wild type strain SJ21R. It was concluded that the SLC1-1 gene suppressed the need to make sphingolipids.

DNA Sequence of the SLC1-1 Gene - A computer search of the base sequence between the EcoRI and the BamHI restriction sites of p411AB/C (FIG. 1) detected only one long open reading frame of 303 codons. Disruption of this open reading frame destroyed suppression activity (p411i#3, FIG. 1) indicating that the open reading frame is part of the SLC1-1 suppressor gene.

The SLC1 gene product (FIG. 2) has a molecular mass of 33,872 daltons, and one transmembrane spanning domain, residues 14 and 30 (VLVVLALAGCGFYGVIA)(SEQ ID NO:9). The sequence can also be predicted by three different algorithms (25–27). Three N-glycosylation and two potential N-myristoylation sites are indicated in FIG. 2.

Comparison of the SLC1 protein with GenBank (release 71) sequences using the FASTA algorithm (28) revealed similarity (FIG. 3) to the PlsC protein of E. coli (13), which is a 1-acyl-sn-glycerol-3-phosphate acyltransferase, and to the ParF protein of Salmonella typhimurium (29). Compared with the bacterial proteins, the SLC1 protein showed 27% identical and 33% similar amino acid residues.

The nucleotide sequence upstream of the SLC1 gene contains an open reading frame (ORFX) oriented in the opposite direction and starting 369 bp upstream of the SLC1 start codon. ORFX contains at least 252 codons (FIG. 2), which encode a protein that does not show homology to protein sequences in the translated GenBank and Swiss-Prot data bases.

Function of the SLC1 Gene Product - The sequence homology data suggest that the SLC1 protein is a 1-acyl-sn-glycerol-3-phosphate acyltransferase, and this idea would be consistent with the appearance of novel glycerol lipids containing a sn-2 $C_{26}$ fatty acid in strains carrying the SLC1-1 suppressor gene.

Figure 4:
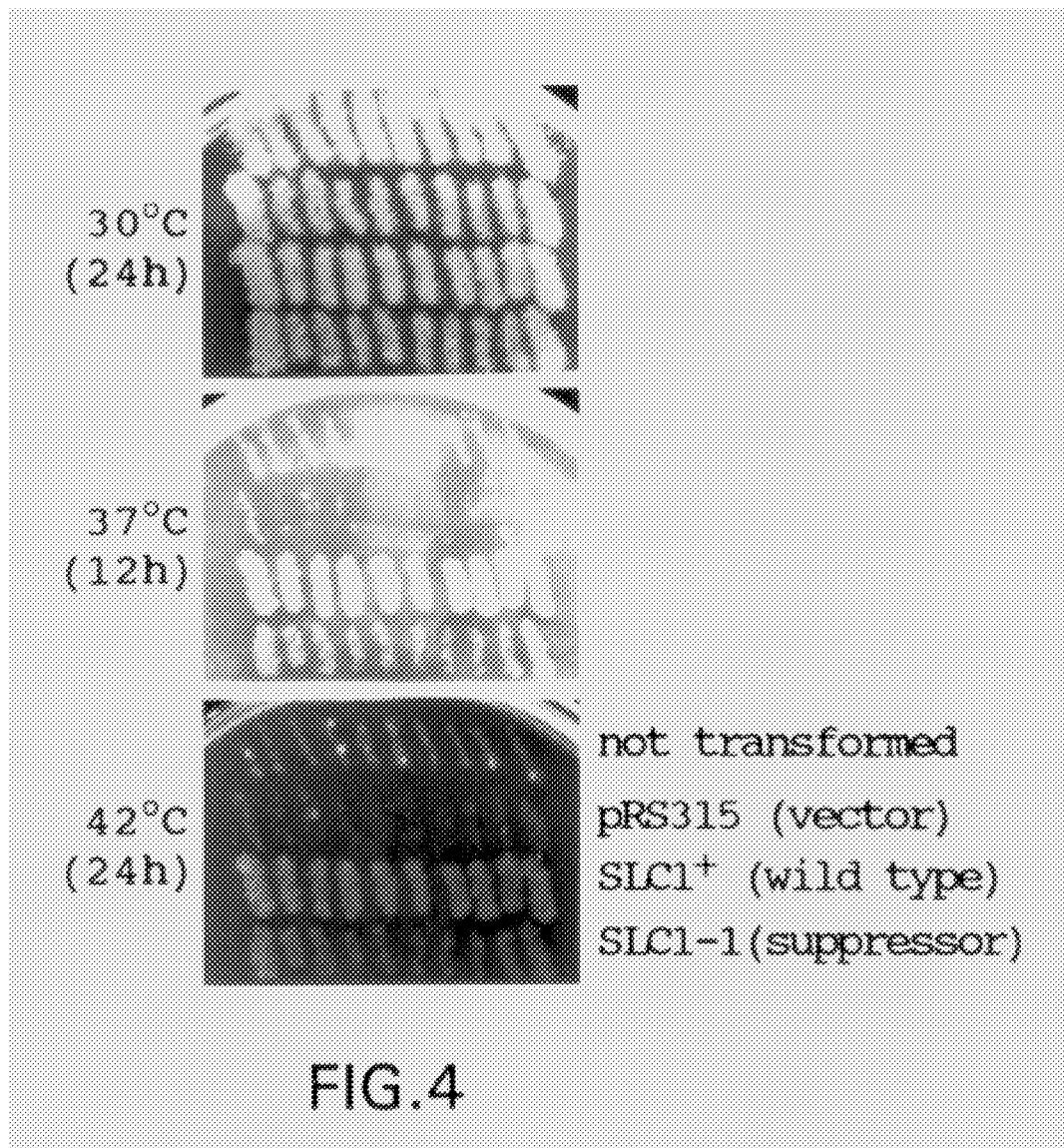
FIG. 4 shows SLC1 gene complements *E. coli* mutant. *E. coli* strain JC201, carrying a temperature-sensitive mutation in the plsC gene, was transformed with the vector pRS315, or the vector carrying a 4.15-kb BamHI fragment containing the yeast wild type SLC1$^+$ gene, or the suppressor allele SLC1-1. Colonies of each type of transformant were streaked onto LB plates and tested for growth at the indicated temperature. The length of incubation in hours is indicated.

To determine if the SLC1 protein contained acyltransferase activity, the SLC1 gene was tested for its ability to complement the plsC mutation in E. coli strain JC201. The plsC mutation causes the strain to grow slowly at 37° C. and almost not at all at 42° C. (13). Both the wild type and the SLC1-1 suppressor allele complemented the plsC mutation and enabled the strain to grow at a nearly normal rate at 37° C. (FIG. 4). The wild type SLC1 allele promoted strong growth at 42° C. while the suppressor allele gave weak growth (FIG. 4). These data suggest that both the wild type SLC1 protein and that encoded by the SLC1-1 suppressor allele possess 1-acyl-sn-glycerol-3-phosphate acyltransferase activity.

To verify this possibility 1-acyl-sn-glycerol-3-phosphate acyltransferase activity was measured in extracts of strain JC201 transformed with a vector alone or with a plasmid bearing either the wild type SLC1+ or the suppressor SLC1-1 gene. Negligible to barely detectable enzyme activity was observed in either the total extract or the total membrane fraction (Table III). As shown by Coleman (22) and verified here (Table III), strain JC201 had little or no enzyme activity compared with wild type cells (JC200) even when assayed at the permissive temperature. Thus the lack of enzyme activity in JC201 carrying either SLC1 allele may mean that the SLC1 protein does not survive cell breakage or is inactivated by the assay conditions as is the case for the temperature-sensitive PlsC enzyme.

TABLE III

1-Acyl-sn-glycerol-3-phosphate acyltransferase activity in *E. coli* strains
Relative activity is expressed as a percentage of wild type cells (JC200). For the homogenate, roughly equal amounts of phosphatidic acid and diacylglycerol were formed; the total rate of acylation for the JC200 homogenate was 73 pmol/min/mg of protein. For the membranes, a negligible amount of diacylglycerol was formed; the rate of phosphatidic acid formation with JC200 membranes was 270 pmol/min/mg of protein.

| Enzyme source | Acyltransferase activity | |
|---|---|---|
| | Homogenate | Membranes |
| | % | |
| JC200 (plsC+) | 100 | 100 |
| JC201 (plsC + vector) | 5 | 0 |
| JC201 (plsC + SLC1+) | 6 | 3 |
| JC201 (plsC + SLC1-1) | ND* | 0 |

*ND, not determined.

Figure 5:
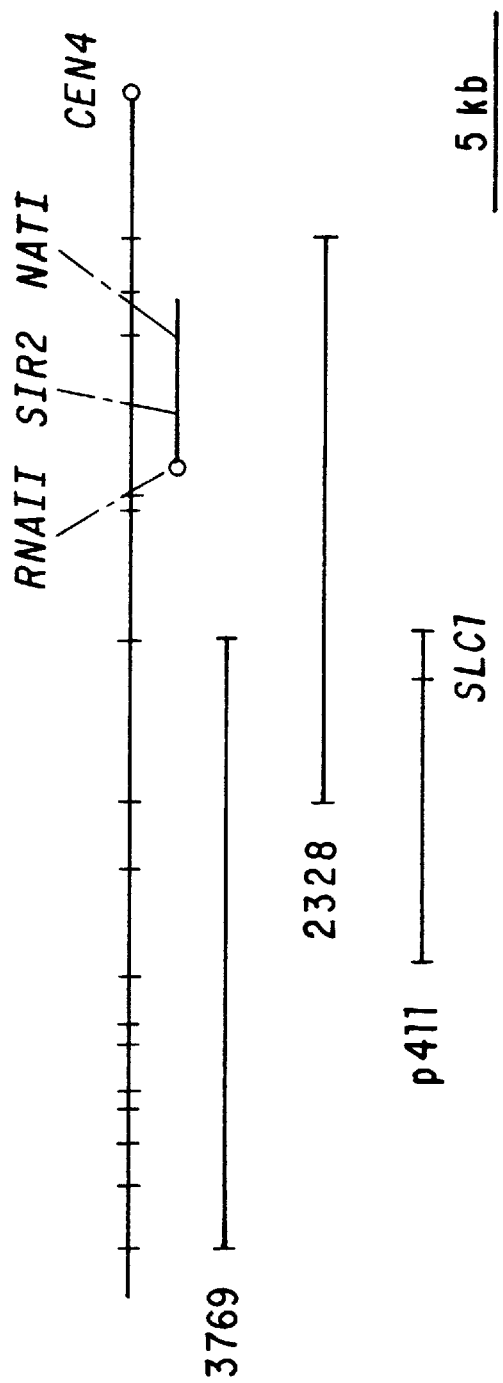
FIG. 5 shows the chromosomal location of SLC1. A restriction map of a portion of the left arm of chromosome IV is depicted at the top of the figure. The map was constructed by overlapping λ clones carrying *S. cerevisiae* DNA inserts (30). Vertical lines indicate EcoRI or HindIII restriction sites used to order and overlap λ clones. Unordered restriction fragments are bound by short vertical lines. The alignment of two λ clones, 3769 and 2328, and the *S. cerevisiae* DNA insert in p411 is shown.

Chromosomal Mapping of SLC1 - The SLC1 gene was mapped to chromosome IV by hybridization of an 886-bp EcoRI-NsiI restriction fragment carrying SLC1 to a Southern blot of separated yeast chromosomes (data not shown). The location of the SLC1 locus on chromosome IV was established by hybridization to a set of λ clones whose insert sequence had been mapped and ordered on the *S. cerevisiae* genome (30). The SLC1 probe hybridized to two overlapping λ clones (clones 3769 and 2328) located on the left arm of chromosome IV, 80 kb from the centromere (FIG. 5). λ clone 2328 also contains the RNA11, SIR2, and NAT1 genes; however, the SLC1 sequence does not overlap with the sequence of any of these genes (31).

Cloning and Sequencing of the Wild Type SLC1 Allele

To determine how the SLC1-1 suppressor allele differs from the wild type allele, termed SLC1+, their sequences were compared. The SLC1+ allele was retrieved from the parental strain 1Δ4 using a plasmid integration and allele rescue technique as described under "Experimental Procedures". Comparison of the two sequences revealed only one nucleotide difference; the A at position 131 of the wild type coding sequence is replaced by T in the SLC1-1 suppressor allele. The mutation in the suppressor allele destroys a DdeI restriction site present in the wild type allele. This base difference allows the two alleles to be distinguished by Southern blot analysis of DdeI-digested DNA (see below).

Conversion of the Wild Type SLC1+ Allele to a Suppressor Allele by a Single Base Change - To confirm that the detected single nucleotide difference between the wild type and suppressor SLC1 alleles is responsible for the suppression phenotype, the wild type sequence was mutated at position 131 from an A to a T by site-directed mutagenesis. This mutant allele was introduced into the Lcb− strain 1Δ4 by plasmid transformation with selection for Leu+ cells. Twenty Leu+ cells were chosen at random and tested for the Lcb+ phenotype by streaking onto PYED plates lacking phytosphingosine. All gave the Lcb+ phenotype indicating that the single base change in the wild type SLC1+ allele converted it to a suppressor allele. These results also indicate that the suppressor allele is dominant to the wild type allele present in strain 1Δ4. As expected, the wild type SLC1+ allele did not give Lcb+ transformants. It was concluded that the single nucleotide change at position 131 of SLC1-1, changing a Gln to a Leu, is responsible for its suppressor activity.

Figures 6A, 6B:
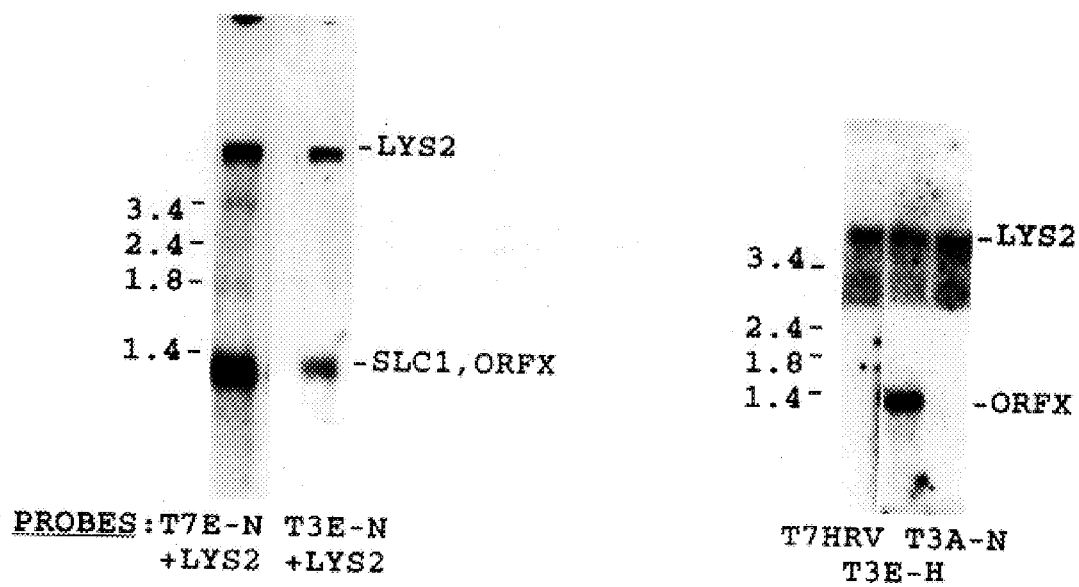
FIGS. 6A–C shows an analysis of SLC1 transcription by Northern blot hybridization. Panel A, each hybridization reaction included an LYS2 probe as an internal control for mRNA concentration. Molecular weight markers and their size in kilobases are indicated at the side of the autoradiograms. Panel B, as in panel A, but after transfer of the RNA to the membrane, the membrane was divided, and each section was hybridized separately with a riboprobe as indicated below each lane. Panel C, restriction map of analyzed region showing the location and 5' to 3' direction of the riboprobes. Open reading frames are shown as an open box. The 3' end of ORFX has not been determined as indicated by the dotted line. The inverted triangle indicates the location of the SLC1-1 suppressor mutation. Wavy lines denote the deduced locations of the two 1.4-kb overlapping transcripts described in the text. The size and orientation of riboprobes (PROBES) are indicated. Restriction endonuclease sites are: A, AatII; Bg, BglII; E, EcoRI; H, HindIII; Hf, HinfI; Ns, NsiI; RV, EcoRV.
Figure 6C:
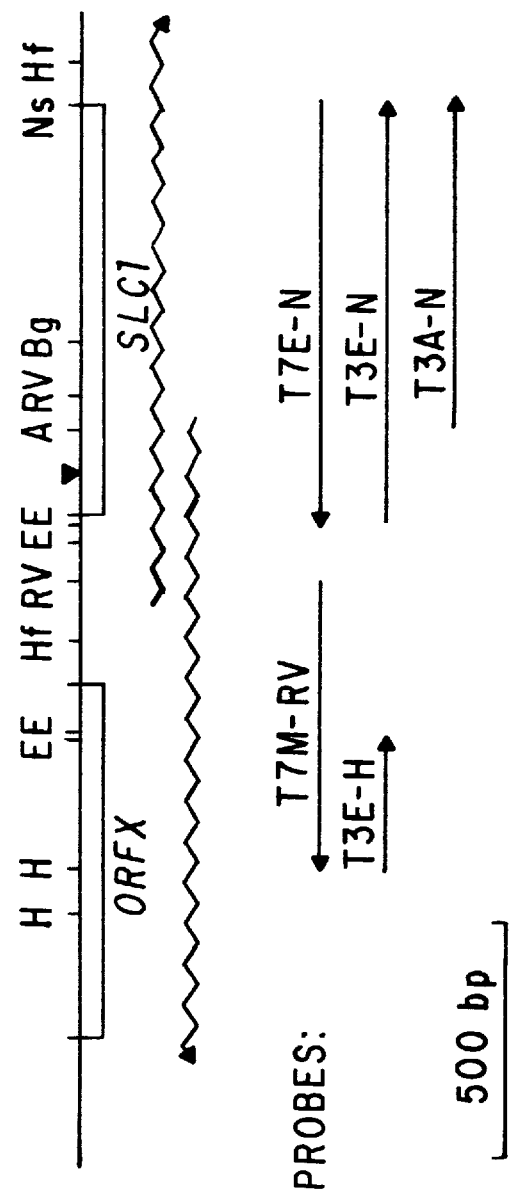

Analysis of SLC1 Transcription - The size of the SLC1 mRNA was determined, and its 5' to 3' orientation was verified using a 920-bp antisense probe (T7E-N) to probe Northern blots of total yeast RNA. The probe detected a 1.4-kb RNA as shown in FIG. 6A. Unexpectedly, probe T3E-N covering the same region of DNA but having the opposite 5' to 3' polarity (colinear with the SLC1 mRNA) also hybridized to a 1.4-kb transcript (FIG. 6B), and probe T3 E-H which did hybridize (FIG. 6B). These data indicate that the 5' end of the 1.4-kb transcript, presumably the ORFX transcript detected by probe T3E-N, is just to the left of probe T3A-N as indicated.

Probe T7H-RV did not hybridize to any transcript (FIG. 6B), whereas probe T3E-H hybridized to a 1.4-kb transcript as expected if ORFX had the 5' to 3' orientation shown. It is not clear whether the suppressor mutation affects only the SLC1 transcript or whether it also possibly affects the ORFX transcript, by changing one nucleotide in the nontranslated leader region.

Figure 7A:
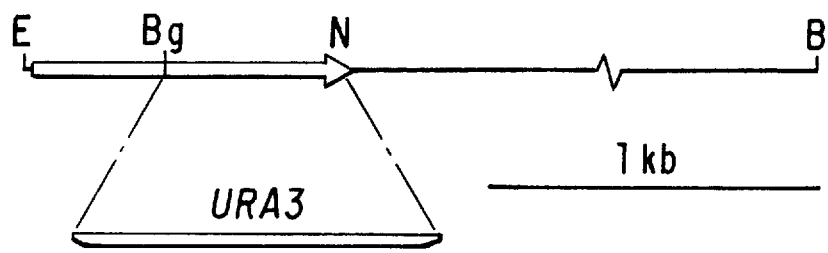
FIGS. 7A–C shows construction of an SLC1 deletion strain. Panel A, diagram of the slc1Δ1::URA3 deletion allele described under "Experimental Procedures." Panel B, Southern blot analysis of the SLC1 locus in diploid strains carrying the deletion allele. Total DNA from six Ura+ diploids transformed with linear plasmid DNA carrying the slc1Δ1::URA3 allele (lanes 1–6) and one Ura+ strain transformed with the vector pRS315 (lane 7) was digested with restriction enzymes EcoRI and BamHI, transferred to a nitrocellulose membrane, and hybridized to a radiolabeled EcoRI-NsiI a SLC1 probe. Lanes 1–6 contain both the wild type SLC1+ (3.4 kb) and the deletion (3.9 kb) alleles, whereas the pRS315 transformation control sample in lane 7 contains only the wild type allele. Panel C, Northern blot analysis of total cellular RNA isolated from wild type strain SJ21R (lane 1) and a haploid spore carrying the slc1Δ1::URA3 allele (lane 2). The blot was hybridized with two different probes: first with the SLC1 anti-sense probe T7E-N (see FIG. 6) an then with probe T3E-N having the opposite 5' to 3' orientation from T7E-N. Molecular weight markers (kb) are shown to the left of the autoradiogram.
Figures 7B, 7C:
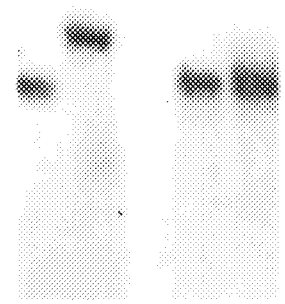

SLC1: Essential for Suppression of the Lcb - Phenotype Not For Vegetative Growth To determine if the SLC1 gene is essential for vegetative growth, an SLC1 deletion allele (slc1Δ::URA3) in which the 3' half of the gene was deleted and replaced by UR3 (FIG. 7A) was constructed. The deletion allele was used to replace one chromosomal copy of SLC1 in a diploid strain (SJ21R/YPH2). Ura+ transformants were analyzed by Southern blotting to verify that the diploid contained one wild type and one deletion allele of SLC1 (FIG. 7B). Tetrad analysis of sporulated diploids showed that all spores in each tetrad analyzed were viable and gave two Ura+ and two Ura− spores. Ura+ spores carrying the slcΔ::URA3 did not display any obvious growth defect when grown on PYED, minimal medium containing nonfermentable carbon sources (glycerol and lactic acid), and at pH 4.1 or at 37° C.

Northern blot analysis was used to verify that the SLC1 mRNA was disrupted by the slc1Δ::URA3 deletion mutation whereas the ORFX mRNA was not. The SLC1-specific probe T7E-N detected a 1.8-kb RNA (FIG. 7C, lane 2), the size expected for the ΔSLC1-URA3 fusion transcript. The ORFX-specific probe T3E-N detected a 1.4 kb RNA, the size expected for the ORFX transcript (FIG. 7C, lane 2). These results suggest that the SLC1 gene is not essential for viability. However, the data do not exclude the possibility that the SLC1-URA3 fusion transcript, which contains the 5' end of the SLC1 transcript, retains SLC1 activity.

Figure 8A:
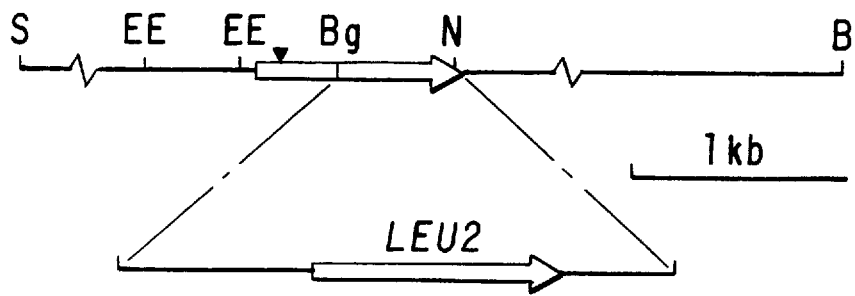
FIGS. 8A–B shows construction of strain 4R3-1 carrying the slc1Δ2::LEU2 deletion allele. The Panel A diagram shows how the slc1Δ2::LEU2 allele was constructed. The location of the SLC1-1 suppressor mutation is indicated by an inverted, filled triangle. Panel B, Southern blot analysis demonstrate that strain 4R3-1 carries the slc1Δ2::LEU2 deletion allele. Chromosomal DNA from the SLC1+ strain 1Δ4 (lane 1), the SLC1-1 strain 4R3 (lanes 2 and 7), and several strains carrying the slc1Δ2::LEU2 allele (lanes 3–6 and 8–11) was digested with restriction enzymes as indicated, separated on a 1.8% agarose gel, transferred to a nylon membrane, hybridized to an EcoRI-NsiI SLC1 anti-sense riboprobe, and autoradiographed. Molecular weight markers (kb) are shown at the sides of the figure.
Figure 8B:
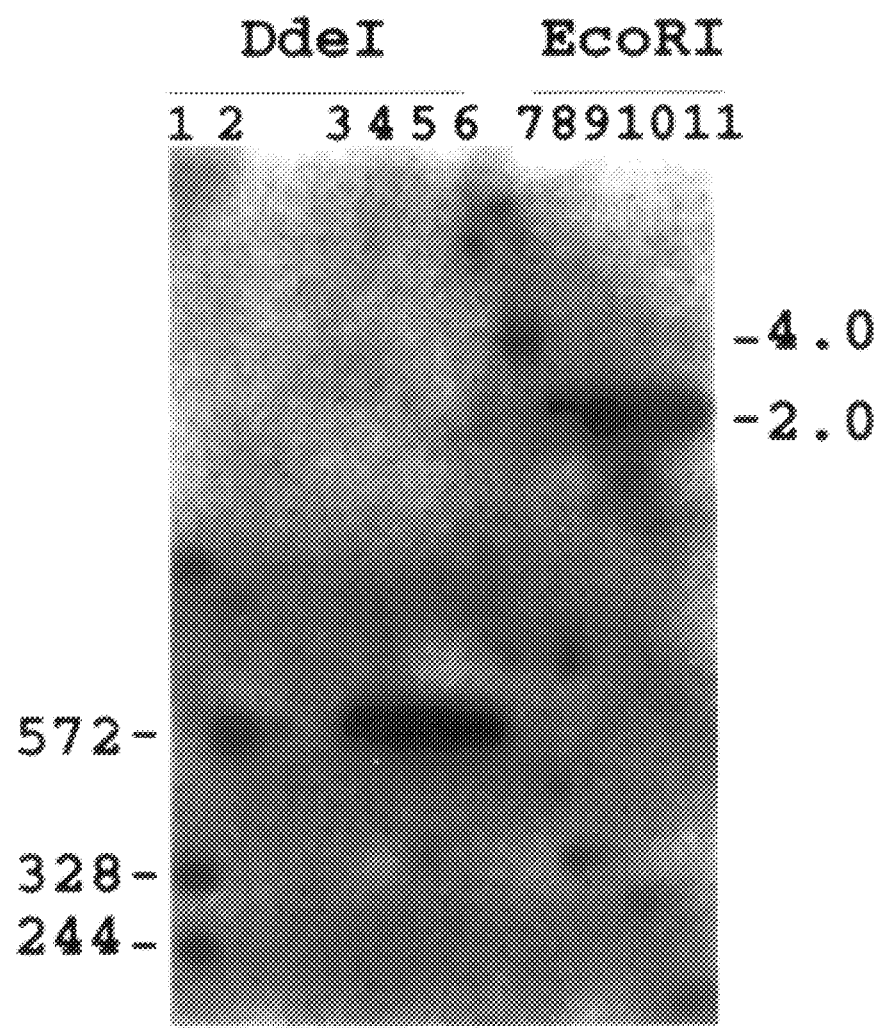

To show that a strain carrying the slc1Δ1::URA3 deletion lacked SLC1 protein activity and to prove that the SLC1 gene and not the ORFX gene is responsible for the suppression phenotype the following alternative experimental approach was used. If the slc1Δ1::URA3 mutation actually inactivated SLC1-1, the gene should no longer function as a suppressor. To examine this hypothesis the 3' half of SLC1-1 in the suppressor strain 4R3 was deleted. The region deleted in SLC1-1 was the same as the region deleted in the slc1Δ1::URA3 allele except that the LEU2 gene was used in place of the URA3 gene (FIG. 8A). The change was made because strain 4R3 is Ura+ and could therefore not be transformed with the slc1Δ1::URA3 allele and selected for Ura+ transformants. The resulting strain, termed 4R3-1, was shown to carry the correct deletion by Southern blot analysis (FIG. 8B). In addition, Northern blot analysis of total RNA revealed that the SLC1 transcript was no longer present, whereas the ORFX transcript remained intact and was produced at the wild type level.

Unlike the parent strain 4R3, strain 4R3-1 was unable to grow on places lacking long chain base, indicating that the strain no longer contained a functional suppressor gene. Thus, the slc1Δ1::LEU2 mutation inactivated suppressor activity (this occurred even though the suppressor mutation at nucleotide 131 was present in the strain). It was concluded that the SLC1 gene and not ORFX is responsible for the suppression phenotype.

SLC strains 4R3 and 7R6 are able to grow without long chain base in the culture medium because of a suppressor mutation. Data show that the suppressor mutation is in a new gene termed SLC1. A single base change at nucleotide 131 (FIG. 2) converts the wild type allele, SLC1+, to the suppressor allele, SLC1-1, thereby changing glutamine 44 to a leucine. How might this single amino acid change allow the cell to bypass the need to make sphingolipids? The suppressor protein could function to bypass the need for sphingolipids by producing a new type of lipid, by overproducing one or more normal lipids, or by creating a variant protein that no longer requires sphingolipids for function.

Pertinent to deciding among these hypotheses is the finding that SLC suppressor strains synthesize novel lipids when grown without a long chain base in the culture medium (12). The suppressor lipids in strains 4R3 and 7R6 comprise a family of related lipids which, like normal sphingolipids have polar head groups containing either phosphoinositol, mannosylphosphoinositol, or mannosyldiphosphoinositol. The polar head groups are attached to mono- and di-fatty acylglycerols instead of ceramide, the acylglycerols containing a $C_{26}$ fatty acid in the sn-2 position. Normally $C_{26}$ fatty acids are found in amide linkage to phytosphingosine to form ceramide and are not found in acylglycerols. These results suggest that the suppressor protein plays a role in synthesis of the suppressor lipids.

A role of the SLC protein in suppressor lipid synthesis was uncovered by comparison of the predicted sequence of the wild type SLC1 or suppressor protein with the translated GenBank. The comparison revealed that the sequences were homologous to the PlsC protein of E. coli (FIG. 3). This protein is a 1-acyl-sn-glycerol-3-phosphate acyltransferase and catalyzes the second step in phospholipid biosynthesis in which a fatty acid is incorporated into the sn-2 position of glycerolipids. Such homology suggests that the SLC1 protein had a similar enzymatic activity. Experimental support for fatty acyltransferase activity was obtained by showing that the wild type and SLC1-1 suppressor genes complemented a temperature-sensitive plsC allele in E. coli and enabled the strain to grow at the restrictive temperature (FIG. 4). Cell-free extracts of such transformed strains did not, however, exhibit acyltransferase activity (Table III), but this result could be because of enzyme inactivation; even the temperature-sensitive E. coli enzyme from strain JC201 is unable to be assayed in extracts (22, Table III).

Next was explored how the SLC1-1 variant protein accounts for the appearance of novel lipids in suppressor strains. One possibility (FIG. 9) is that the SLC1-1 protein is an acyltransferase with an altered substrate specificity that enables it to use a saturated $C_{26}$-CoA, accumulating in the absence of phytosphingosine, instead of the mostly unsaturated $C_{16}$ or $C_{18}$-CoAs used by the wild type protein. The variant protein inserts a $C_{26}$ fatty acid into the sn-2 position of lysophosphatidylinositol to produce a $C_{26}$ fatty acid species of phosphatidyl-inositol, one of the suppressor lipids (12). This product then mimics the normal inositol P-ceramide, being further decorated in turn by mannose and inositol phosphate giving rise to the other suppressor lipids. Alternatively, the variant enzyme could add a $C_{26}$ fatty acid to the sn-2 position of lysophosphatidic acid (1-acylglycerol-3-P), undergo hydrolysis to diacylglycerol species, which would then mimic ceramide and receive the normal sphingolipid-polar head groups; finally monoacylglycerol could serve as an acceptor for a $C_{26}$ fatty acid-forming diacylglycerol. $C_{26}$ fatty acids are found only in suppressor lipids and not in other major glycerolipids such as phosphatidylethanolamine and phosphatidylcholine present in suppressor strains(12). Therefore, if lysophosphatidic acid or monoacylglycerol were a $C_{26}$ fatty acid acceptor, the products formed could not serve as precursors in the synthesis of phosphatidyl-ethanolamine or phosphatidylcholine. Thus, it is proposed that the $C_{26}$ fatty acid acts as a signal for addition of the sphingolipid polar head groups and that the SLC1 gene encodes an sn-2-acylgly-ceride fatty acyltransferase. This is the first such eucaryotic gene to be cloned.

Figure 9:
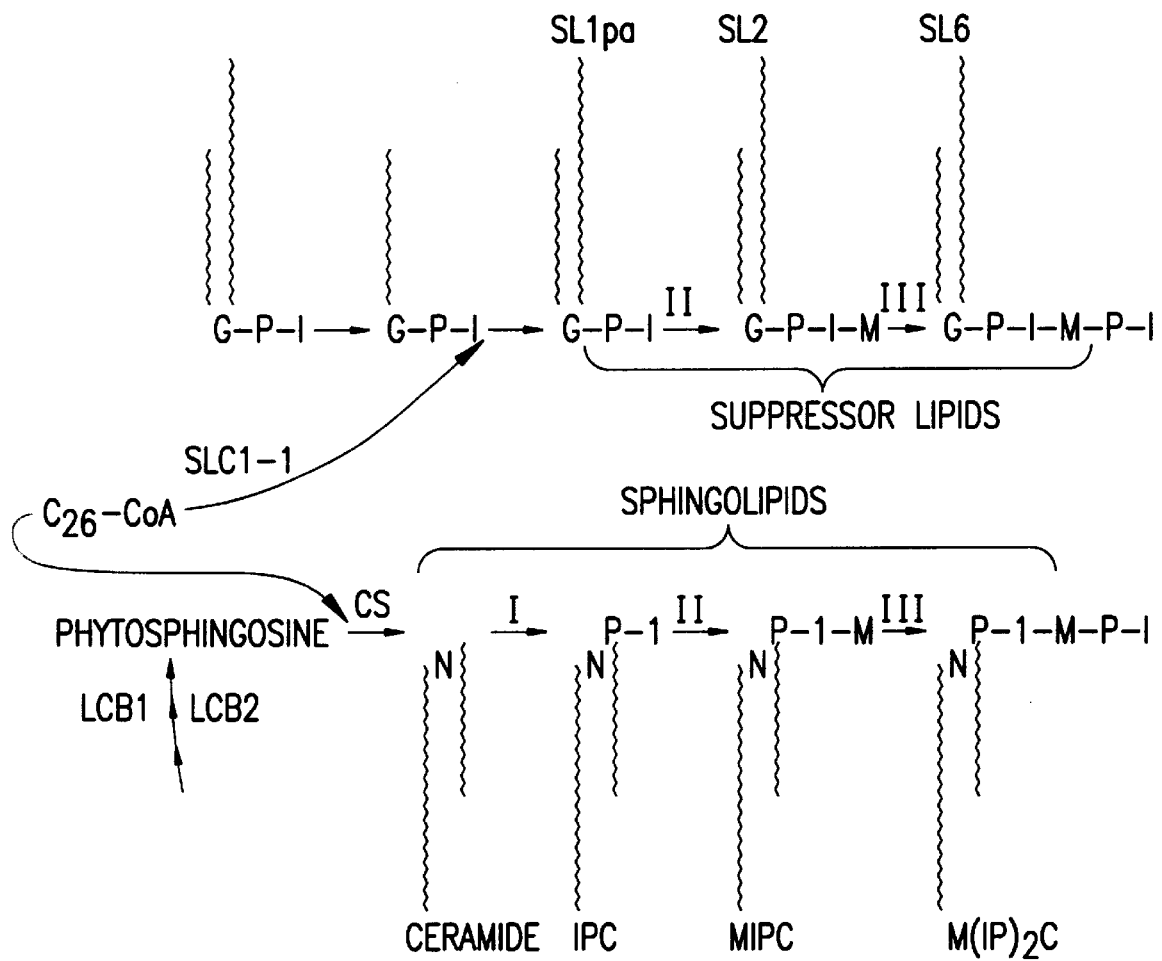
FIG. 9 shows the function of the SLC1-1 gene in the synthesis of suppressor lipids. CS, I, II, III refer to sphingolipid biosynthetic reactions, involving a ceramide synthetase, a phosphoinositol transferase, a mannosyltransferase, and a phosphoinositol transferase, respectively. Other abbreviations: I, inositol; M, Mannose; G, glycerol; P, phosphorus; long wavy lines, $C_{26}$ fatty acyl group; short wavy lines, $C_{16/18}$ fatty acyl groups or $C_{18}$-phytosphingosine; SL designations are as in (12).

Strains carrying the SLC1-1 suppressor gene do not make suppressor lipids when cultured in the presence of a long chain base (12). One explanation for this result is that $C_{26}$ fatty acids are a better substrate for ceramide synthetase (acyl-CoA:phytosphingosine acyltransferase) than for the SLC1-1 protein. Consequently, in the presence of a long chain base the $C_{26}$ fatty acid is preferentially incorporated into ceramide (FIG. 9).

The PlsC protein of E. coli is bound to the inner membrane of the cell (13). Since both the wild type and suppressor SLC1 proteins could substitute for the PlsC protein they too are likely to be membrane-bound both in E. coli and in yeast.

Analysis of the SLC1 protein identified one potential membrane-spanning helix (FIG. 2) which could anchor the protein to a membrane. Like the PlsC and ParF proteins, the SLC1 protein has a large net positive charge (pI=10.15) which is important for interaction with acidic membrane lipids or with an acidic substrate.

It has been noted that all genes for phospholipid biosynthesis in yeast contain an 11-bp inositol/choline-responsive element in their promoter region having the consensus sequence TYTTCACATGY (SEQ ID NO:7)(32). In addition, these elements are found in front of genes that seem to be expressed constitutively including FAS1 and FAS2 coding for fatty acid synthetase (32). Whether inositol/choline-responsive elements respond to choline/inositol control (33) or act constitutively is dependant upon the promoter context.

The present data indicates that the SLC1 protein is involved in acylation of phospholipids. The SLC1 promoter was examined by computer which identified two putative inositol/choline-responsive elements at positions −503/−513 and −746/−756 (FIG. 10). In addition, the SLC1 promoter also contains a sequence at position −145/157 that perfectly matches the Abf1/Baf1 consensus element RTCRYNNNNNACG (SEQ ID NO:10)(34,35). This element is also present in the FAS1 and FAS2 promoters.

Ceramide and related breakdown products of sphingolipid turnover have been implicated as second messengers in higher eucaryotic cells (36, 37). At this time there is no evidence for a similar function in S. cerevisiae. SLC strains 4R3, 7R4, and 7R6 are useful in studying ceramide function since the strains can be manipulated to either make or lack ceramide. Suppressor strains lacking ceramide are able to grow vegetatively and mate, so ceramide must not be essential for these cellular functions or else the suppressor lipids present in suppressor strains are able to substitute for ceramide, which seems unlikely. Suppressor strains lacking ceramide do show abnormal behavior since they cannot grow at low pH, at elevated temperature, or in the presence of a high concentration of salt or glycerol (38). Strains and plasmids mentioned in the disclosure are available from the University of Kentucky.

Example- Plant transfection

With this new knowledge of the identification and function of the SLC1 gene, the SLC1 gene or specifically altered mutant versions are incorporated in plants and animals, preferably those used for food. Since the SLC1 gene and its protein product is a 1-acyl-sn-glycerol-3-phosphate acyltransferase, it catalyzes the second step in phospholipid biosynthesis in which a fatty acid is incorporated into the sn-2 position of glycerolipids.

The gene or homologs of it isolated from another organism can be incorporated in a vector containing a promoter and/or other regulatory sequence which would cause the gene to be expressed. Vectors are constructed by methods known in the art, for example, as set forth in Chapter 9 of *Molecular Cloning: A Laboratory Manual,* Second Edition, Sambrook et al., Cold Spring Harbor Press (1989) incorporated herein by reference in its entirety.

For example, the SLC1 gene, one of its mutated variants, or a plant homologue, is transfected into plant tissue and used to produce a transgenic. The gene is ligated to a plant promoter, for example the cauliflower mosaic virus (CaMV) 35S promoter (Odell et al., *Nature,* 313 (6005):810–812, Feb. 28, 1985; incorporated herein by reference in its entirety) and introduced into plant cells as described by Broglie et al., (Science, 1984, 224:838–842; incorporated herein by reference in its entirety). Vector construction may be accomplished by methods known in the art, for example as outlined in *Molecular Cloning: A Laboratory Manual,* Second Edition, Sambrook et al., Cold Spring Harbor Press (1989) incorporated herein by reference in its entirety. The transfected gene and its product, for example, can result in more insertions of a different fatty acid into the sn-2 position of glycerolipids.

Example-Animal

Another example inserts the SLC1 gene, one of its mutated variants, or an animal (species-specific) homolog into the genome of economically important domesticated animals. There are two general approaches that may be used. In one, the gene and its regulatory sequences is inserted randomly into the genome of the host organism. In the other approach, the gene is targeted to a specific chromosomal locus and integrated by homologous recombination. The SLC1 gene, specifically the coding region, would be connected to a promoter and other regulatory sequence that are able to express genes in the desired type of cell. An example of such a promoter sequence being CMV (human cytomegalovirus, present for example in the pcDNA3 and pRc/CMV vectors available commercially from Invitrogen, San Diego, Calif.). The pcDNA3 and pRc/CMV vectors may be used for random integration by selecting cells for resistance to the antibiotic G418. Procedures for transfecting vector DNA into cells and for selecting antibiotic resistant transfectants are described in Chapter 16 of *Molecular Cloning: A Laboratory Manual,* Second Edition, Sambrook et al. 1989). Procedures and vectors for gene targeting are described in the paper by Detloff et al., (1994, Molecular and Cellular Biology 14:6936–6943; incorporated herein by reference in its entirety).

The gene can be manipulated as discussed above, to allow for growth of plant material or animal, such as domesticated animals used as food, which comprises glycerolipids with more fatty acids in the sn-2 position altered with respect to chain length and/or unsaturation.

Fatty acids produced by the recombinant plant and animal material of the invention can be detected by the methods known in the art, for example by chromatographic methods as set forth in Lester, R. L., Wells, G. B., Oxford, G., and Dickson, R. C. (Jan. 15, 1993) *J. Biol. Chem.* 269, 845–856 at page 851, incorporated herein by reference in its entirety.

Alternatively, the gene, or relevant portions thereof, or its protein product and sense or antisense sequences thereto, can be labelled by methods known in the art (see, for example, as outlined in *Molecular Cloning: A Laboratory Manual,* Second Edition, Sambrook et al., Cold Spring Harbor Press (1989) incorporated herein by reference in its entirety, and used as a probe for the detection of homologous gene sequences in other organisms. The probe can incorporate a detectable label for example, selected from chromophores, fluorophores, chemiluminescent materials and radioisotopes. Probes can be used to determine whether the plant or animal food contains the gene of interest for the production of glycerolipids with more fatty acids in the sn-2 position altered with respect to chain length and/or unsaturation. Portions of the gene may also be used as primers for polymerase chain reaction.

REFERENCES

1. Hakomori, S. (1983) in *Handbook of Lipid Research* (Kanfer, J. N., and Hakomori, S., eds) Vol. 3, pp. 1–165, Plenum Publishing Corp., New York.
2. Hannun, Y. A., and Bell, R. M. (1989) *Science* 243, 500–507.
3. Hakomori, S. (1990) *J. Biol. Chem.* 265, 18713–18716.
4. Smith, S. W., and Lester, R. L. (1974) *J. Biol. Chem.* 249, 3395–3405.
5. Steiner, S., Smith, S., Waechter, C. J., and Lester, R. L. (1969) *Proc. Natl. Acad. Sci. U.S.A.* 64, 1042–1048.
6. Merrill, A. H., Jr., and Jones, D. D. (1990) *Biochim. Biophys Acta.* 1044, 1–12.
7. Buede, R., Rinker-Schafer, C., Pinto W. J., Lester, R. L., and Dickson, R. C. (1991) *J. Bacteriol.* 173, 4325–4332.
8. Wells, G. B., and Lester, R. L. (1983) *J. Biol. Chem.* 258, 10200–10203.
9. Pinto, W. J., Srinivasan, B., Shepherd, S., Schmidt, A., Dickson, R. C., and Lester, R. L. (1992) *J. Bacteriol.* 174, 2565–2574.
10. Pinto, W. J., Wells, G. W., and Lester, R. L. (1992) *J. Bacteriol.* 174, 2575–2581.
11. Dickson, R. C., Wells, G. B., Schmidt, A., and Lester, R. L. (1990) *Mol. Cell. Biol.* 10, 2176–2181.
12. Lester, R. L., Wells, G. B., Oxford, G., and Dickson, R. C. (Jan. 15, 1993) *J. Biol. Chem.* 269, 845–856.
13. Coleman, J. (1992) *Mol. & Gen. Genet.* 232, 295–303.
14. Strathern, J. N., and Higgins, D. R. (1991) *Methods Enzymol.* 194, 319–329.
15. Ma, H., Kunes, S., Schatz, P. J., and Botstein, D. (1987) Gene (Amat.) 58, 201–216.
16. Stiles, J. I., Szostak, J. W., Young, A. T., Wu, R., Consaul, S., and Sherman, F. (1981) *Cell* 25, 277–284.

17. Sikorski, R. S., and Hieter, P. (1989) *Genetics* 122, 19–27.
18. Carlson, M., and Botstein, D. (1982) *Cell* 28, 145–154.
19. Kuzhandaivelu, N., Jones, W. K., Martin, A. K., and Dickson, R. C. (1992) *Mol. Cell. Biol.* 12, 1924–1931.
20. Barnes, D. A., and Thorner, J. (1986) *Mol. Cell. Biol.* 6, 2828–2838.
21. Rothstein, R. J. (1983) *Methods Enzymol.* 101, 202–211.
22. Coleman, J. (1990) *J. Biol. Chem.* 265, 17215–17221.
23. Kawaguchi, A., Yoshimura, T., and Okuda, S. (1981) *J. Biochem.* 89, 337–339.
24. Steiner, M. R., and Lester, R. L. (1972) *Biochim. Biophys. Acta* 260, 222–243.
25. Klein, P., Kanehisa, M., and DeLisi, C. (1985) *Biochim. Biophys. Acta* 815, 468–476.
26. Eisenberg, D., Schwarz, E., Komaromy, M., and Wall, R. (1984) *J. Mol. Biol.* 179, 125–142.
27. Rao, M. J. K., and Argos, P. (1986) *Biochim. Biophys. Acta* 869, 197–214.
28. Pearson, W. R., and Lipman, D. J. (1988) *Proc. Natl. Acad. Sci. U.S.A.* 85, 2444–2448.
29. Luttinger, A. L., Springer, A. L., and Schmid, M. B. (1991) *New Biologist* 3, 687–697.
30. Olsen, M. V., Dutahik, J. E., Graham, M. Y., Broudeur, G. M., Helms, C., Frank, M., MacCollin, M., Scheinman, R., and Frank, T. (1986) *Proc. Natl. Acad. Sci. U.S.A.* 83, 7826–7830.
31. Mullen, J. R., Kayne, P. S., Moerschell, R. P., Tsunasawa, S., Griboskov, M., Colavito-Shepanski, M., Grunstein, M., Sherman, F., and Sternglanz, R. (1989) *EMBO J.* 8, 2067–2075.
32. Schuller, H. J., Hahn, A., Troster, F., Schutz, A., and Schweizer, E. (1992) *EMBO J.* 11, 107–114.
33. Nikoloff, D. M., and Henry, S. A. (1991) *Annu. Rev. Genet.* 25, 559–583.
34. Dorsman, J. C., Doorenbosch, M. M., Maurer, C. T. C., de Winde, J. H., Mager, W. H., Planta, R. J., and Grivell, L. A. (1989) *Nucleic Acids Res.* 17, 4917–4923.
35. Halfter, H., Muller, U., Winnacker, E. L., and Gallwitz, D. (1989) *EMBO J.* 8, 3029–3037.
36. Dobrowsky, R. T., and Hannun, Y. A. (1992) *J. Biol. Chem.* 267, 5048–5051.
37. Dressier, K. A., Mathias, S., and Kolesnick, R. N. (1992) *Science* 255, 1715–1718.
38. Patton, J. L., Srinivasan, B., Dickson, R. C., and Lester, R. L. (1992) *J. Bacteriol.* 174, 7180–7184.
39. Higgins, D. G., and Sharp, P. M. (1988) *Gene* (Amst.) 73, 237–244.
40. Johnston, S. A., and Hopper, J. E. (1982) *Proc. Natl. Acad. Sci. U.S.A.* 79, 6871–6975.

The purpose of the above description and examples is to illustrate some embodiments of the present invention without implying any limitation. It will be apparent to those of skill in the art that various modifications and variations may be made to the composition and method of the present invention without departing from the spirit or scope of the invention. All patents, publications and references cited herein are incorporated by reference in their entireties.

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 3244 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 1125..2036

( x i ) SEQUENCE DESCRIPTION: SEQ ID NO:1:

```
CTTCTTATTT  TTGGGGAATT  TAGGCAAGTT  TTTCTTCTTA  TGGCCGTTAA  AGGATCTTGA      60

TCTACCGCTG  AAGTTTTGG   ACTTCGAGGC  CTCTCTCTGT  AAATCAAACT  GTTTTTTCGT     120

CAAAACACTC  AGTTTCTTAC  CTTCATATGA  CAAATTTCG   TTGGACTCAT  CGTCATTGGA     180

ATACGATTTC  AAAAAAGCTT  CACATTCTGG  AATTGTCTTA  AATTCCACCA  AGACCGTACC     240

ATTAAATTTC  TTGTTTCTGT  GATCTCTTCT  CAAACGCACT  TGGTTGATTT  CACCTAATTT     300
```

```
TTTGAAAAAG  GCTTCCAAGT  TCTCCTGCAA  TTCTGGAATT  TGGGAAGCTT  CAACGTCCTC    360

ATGTGGGAAA  TTCATTACAG  CCAAAGTCCG  TTGGTTTTGC  TCAATTCTGG  CATTTCTGGC    420

AGCAGTTAGG  TCCAAAGGAA  CACGTCTCTT  GACGTTCTCT  CCATCAGCAG  ATACTTCCAA    480

AATTTCAGAA  CTACGTAGTG  CTTCGATAAC  CTTATCCACT  GGTCTATATT  TCTTCATACG    540

GTTGAATGTG  GCGATGGTGC  TGATGGGGAC  CCATCCATCG  TTTTTTTCCG  CTGTTGTGCG    600

CAAGAACCTG  TCATATGGAA  AGTTGAATTC  AGAAAGTAG   AATTCCACTT  GCTTTAAACA    660

TCTGTCCAAG  ACTTCTGGAG  TAAATTCAAT  CACAGCAAAT  GAATTACGTC  TTGATTGTGG    720

TTTCTCTTGC  TCCTCTTGTT  GTGGTTTTTC  AGACATTACT  TCTTTGCAGA  TGCTACTTTA    780

GTTCCAGTAG  AACCAAATAG  AACCCATTTT  TTGGAAAAAG  AAAAAAATAC  ATCATAGCGA    840

TGAGATGCGA  CTCTGTGCTT  TTGATTTGGT  TGTAATTCAA  AAATCTTGAG  ATATTGCGAT    900

GAGGTTGGGC  TGAACACATT  ACACTAAGAC  GAAGACGAAA  ATTTTTTCAC  GGTCACGAGA    960

TGGATCTCGT  GAATGATGAT  ATCAATTATG  CTTCCTTTGT  TTTGTTGAGA  ATATGGTATG   1020

GTGTTCAAAA  TACTTATATT  AGGAAGGGTT  TAAGGTGAAG  GGGGAATTCT  TCAATAGAGA   1080

AGTTTAGTGG  TTTCCCTCCG  TCAGTGAATT  CGAGCAAAAA  ATAATGAGT   GTGATAGGTA   1140

GGTTCTTGTA  TTACTTGAGG  TCCGTGTTGG  TCGTACTGGC  GCTTGCAGGC  TGTGGCTTTT   1200

ACGGTGTAAT  CGCCTCTATC  CTTTGCACGT  TAATCGGTAA  GCAACATTTG  GCTCAGTGGA   1260

TTACTGCGCG  TTGTTTTTAC  CATGTCATGA  AATTGATGCT  TGGCCTTGAC  GTCAAGGTCG   1320

TTGGCGAGGA  GAATTTGGCC  AAGAAGCCAT  ATATTATGAT  TGCCAATCAC  CAATCCACCT   1380

TGGATATCTT  CATGTTAGGT  AGGATTTTCC  CCCTGGTTG   CACAGTTACT  GCCAAGAAGT   1440

CTTTGAAATA  CGTCCCCTTT  CTGGGTTGGT  TCATGGCTTT  GAGTGGTACA  TATTTCTTAG   1500

ACAGATCTAA  AAGGCAAGAA  GCCATTGACA  CCTTGAATAA  AGGTTTAGAA  AATGTTAAGA   1560

AAAACAAGCG  TGCTCTATGG  GTTTTTCCTG  AGGGTACCAG  GTCTTACACG  AGTGAGCTGA   1620

CAATGTTGCC  TTTCAAGAAG  GGTGCTTTCC  ATTTGGCACA  ACAGGGTAAG  ATCCCCATTG   1680

TTCCAGTGGT  TGTTTCCAAT  ACCAGTACTT  TAGTAAGTCC  TAAATATGGG  GTCTTCAACA   1740

GAGGCTGTAT  GATTGTTAGA  ATTTTAAAAC  CTATTTCAAC  CGAGAACTTA  ACAAAGGACA   1800

AAATTGGTGA  ATTTGCTGAA  AAAGTTAGAG  ATCAAATGGT  TGACACTTTG  AAGGAGATTG   1860

GCTACTCTCC  CGCCATCAAC  GATACAACCC  TCCCACCACA  AGCTATTGAG  TATGCCGCTC   1920

TTCAACATGA  CAAGAAAGTG  AACAAGAAAA  TCAAGAATGA  GCCTGTGCCT  TCTGTCAGCA   1980

TTAGCAACGA  TGTCAATACC  CATAACGAAG  GTTCATCTGT  AAAAAAGATG  CATTAAGCCA   2040

CCACCACATT  TTTAGAGTAG  TATATAGACC  CAAAAACTGT  AATTATCTTT  TAAAAAAGT   2100

AAAATGACTT  ACGAATGATT  CTGATGATTT  TATTTATTAC  GACTCATATA  CCCAGCGTAA   2160

GAAGTGATCA  ATAGACCGCT  ACTTTATTCG  GAGAAAGAGA  AAAGAACTTT  CCATTGTAAT   2220

GTATATATAA  CACCAGGCAT  GTGTCAAAAA  TGTGAGACTA  AATAGAAAGA  AAAATACGAG   2280

GAACAACAAA  TAATACGATC  TTGTGCATAT  TTTTTCCCTT  TTTTTTTTA   ATTCTTTTT    2340

TCTGAAATTT  TTCATTTGTT  CACTGTTTAA  TATCTATCCA  TTTTTGTTTC  CGAATTTTCA   2400

TTAACTTTAT  TACTTATTTA  CGATACAATT  TTCCCTTTAA  TCTAGTACGA  AATGACAACA   2460

ACCTCAACAA  CCAGTGTAGA  TGGCAGAACC  TCCTCGACTT  TGAAGGCTAC  TTTATCTGCT   2520

TCAGGTCCAA  ATTCAAATGG  TCCAACGCCC  GCTGTGCTTC  CTCAGAAGCC  AAAATTAACA   2580

GGTTGGGCGC  AGGCAGCTGC  CAAAGCCCTT  CCAAGGCAAC  AGCAACAGCA  ACAGCAGGCA   2640

CGAAAAGATG  ATTCCGTGGC  TGTACAACCT  GCTAATACGA  AGACTAAAAC  CATCGCATCT   2700
```

```
ACCGCGCCGC CTGCTAATAT AAAGGGTAGT TCCACCGCCA ATGGATCATC CACAAATAAG      2760

AAATTTAAAA GAGCGAATAA ACAACCTTAC AATAGAGAAG AAGTTAGATC GTATATGCAC      2820

AAATTATTTC AGAGCTATAC CGCTGGTGAA AAAAGTCATT CAATGAAAAC TTATAAGCAA      2880

GTACTATCAG AAACGGCAAG TGGCAGAGTT TCAACAGCCA CTGACTGGGG TACTGTATCA      2940

AGCAGTAAAA ATAAGAATAA AAAATACGGC TGTTTGTCCG ATATTGCTAA AGTTTTAAGA      3000

AACCAATGAG AATATCGAAG CATCACGTTT CATAACGCAA AAAGGAGTCA AACAAAAAAT      3060

GAAGTATGAA GTCAAGAAAA CGAAGAAAAG AGGAAAATAG AAGAAATGAA AATATTATTT      3120

TACAAGCGTA AATAAAAATT TTATAATTCA TAATGTCGAA AAATGTATAC TGTGTTAAGA      3180

CGCCTTTCTT TGCTTTTTCT CTTAGTCTTT ATTGCATAGT TCACTTAGCC TTTCCGATGC      3240

TAGC                                                                  3244
```

( 2 ) INFORMATION FOR SEQ ID NO:2:

( i ) SEQUENCE CHARACTERISTICS:
        ( A ) LENGTH: 303 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:2:

```
Met Ser Val Ile Gly Arg Phe Leu Tyr Tyr Leu Arg Ser Val Leu Val
 1               5                  10                  15

Val Leu Ala Leu Ala Gly Cys Gly Phe Tyr Gly Val Ile Ala Ser Ile
                20                  25                  30

Leu Cys Thr Leu Ile Gly Lys Gln His Leu Ala Gln Trp Ile Thr Ala
            35                  40                  45

Arg Cys Phe Tyr His Val Met Lys Leu Met Leu Gly Leu Asp Val Lys
        50                  55                  60

Val Val Gly Glu Glu Asn Leu Ala Lys Lys Pro Tyr Ile Met Ile Ala
65                  70                  75                  80

Asn His Gln Ser Thr Leu Asp Ile Phe Met Leu Gly Arg Ile Phe Pro
                85                  90                  95

Pro Gly Cys Thr Val Thr Ala Lys Lys Ser Leu Lys Tyr Val Pro Phe
               100                 105                 110

Leu Gly Trp Phe Met Ala Leu Ser Gly Thr Tyr Phe Leu Asp Arg Ser
           115                 120                 125

Lys Arg Gln Glu Ala Ile Asp Thr Leu Asn Lys Gly Leu Glu Asn Val
       130                 135                 140

Lys Lys Asn Lys Arg Ala Leu Trp Val Phe Pro Glu Gly Thr Arg Ser
145                 150                 155                 160

Tyr Thr Ser Glu Leu Thr Met Leu Pro Phe Lys Lys Gly Ala Phe His
               165                 170                 175

Leu Ala Gln Gln Gly Lys Ile Pro Ile Val Pro Val Val Ser Asn
           180                 185                 190

Thr Ser Thr Leu Val Ser Pro Lys Tyr Gly Val Phe Asn Arg Gly Cys
       195                 200                 205

Met Ile Val Arg Ile Leu Lys Pro Ile Ser Thr Glu Asn Leu Thr Lys
210                 215                 220
```

```
Asp  Lys  Ile  Gly  Glu  Phe  Ala  Glu  Lys  Val  Arg  Asp  Gln  Met  Val  Asp
225                      230                      235                      240

Thr  Leu  Lys  Glu  Ile  Gly  Tyr  Ser  Pro  Ala  Ile  Asn  Asp  Thr  Thr  Leu
               245                      250                          255

Pro  Pro  Gln  Ala  Ile  Glu  Tyr  Ala  Ala  Leu  Gln  His  Asp  Lys  Val
               260                      265                     270

Asn  Lys  Lys  Ile  Lys  Asn  Glu  Pro  Val  Pro  Ser  Val  Ser  Ile  Ser  Asn
          275                      280                     285

Asp  Val  Asn  Thr  His  Asn  Glu  Gly  Ser  Ser  Val  Lys  Lys  Met  His
          290                      295                     300
```

(2) INFORMATION FOR SEQ ID NO:3:

(i) SEQUENCE CHARACTERISTICS:
      (A) LENGTH: 245 amino acids
      (B) TYPE: amino acid
      (C) STRANDEDNESS: single
      (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:3:

```
Met  Leu  Tyr  Ile  Phe  Arg  Leu  Ile  Ile  Thr  Val  Ile  Tyr  Ser  Ile  Leu
1                   5                        10                      15

Val  Cys  Val  Phe  Gly  Ser  Ile  Tyr  Cys  Leu  Phe  Ser  Pro  Arg  Asn  Pro
               20                       25                      30

Lys  His  Val  Ala  Thr  Phe  Gly  His  Met  Phe  Gly  Arg  Leu  Ala  Pro  Leu
          35                       40                      45

Phe  Gly  Leu  Lys  Val  Glu  Cys  Arg  Lys  Pro  Thr  Asp  Ala  Glu  Ser  Tyr
     50                       55                      60

Gly  Asn  Ala  Ile  Tyr  Ile  Ala  Asn  His  Gln  Asn  Asn  Tyr  Asp  Met  Val
65                       70                      75                       80

Thr  Ala  Ser  Asn  Ile  Val  Gln  Pro  Pro  Thr  Val  Thr  Val  Gly  Lys  Lys
                85                       90                      95

Ser  Leu  Leu  Trp  Ile  Pro  Phe  Phe  Gly  Gln  Leu  Tyr  Trp  Leu  Thr  Gly
               100                      105                     110

Asn  Leu  Leu  Ile  Asp  Arg  Asn  Asn  Arg  Thr  Lys  Ala  His  Gly  Thr  Ile
          115                      120                     125

Ala  Glu  Val  Val  Asn  His  Phe  Lys  Lys  Arg  Arg  Ile  Ser  Ile  Trp  Trp
     130                      135                     140

Phe  Pro  Glu  Gly  Thr  Arg  Ser  Arg  Gly  Arg  Gly  Leu  Leu  Pro  Phe  Lys
145                      150                     155                      160

Thr  Gly  Ala  Phe  His  Ala  Ala  Ile  Ala  Ala  Gly  Val  Pro  Ile  Ile  Pro
               165                      170                     175

Val  Cys  Val  Ser  Thr  Thr  Ser  Asn  Lys  Ile  Asn  Leu  Asn  Arg  Leu  His
               180                      185                     190

Asn  Gly  Leu  Val  Ile  Val  Glu  Met  Leu  Pro  Pro  Ile  Asp  Val  Ser  Gln
          195                      200                     205

Tyr  Gly  Lys  Asp  Gln  Val  Arg  Glu  Leu  Ala  Ala  His  Cys  Arg  Ser  Ile
     210                      215                     220

Met  Glu  Gln  Lys  Ile  Ala  Glu  Leu  Asp  Lys  Glu  Val  Ala  Glu  Arg  Glu
225                      230                     235                      240

Ala  Ala  Gly  Lys  Val
               245
```

( 2 ) INFORMATION FOR SEQ ID NO:4:

( i ) SEQUENCE CHARACTERISTICS:
        ( A ) LENGTH: 245 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:4:

```
Met Leu Tyr Ile Phe Arg Leu Ile Val Thr Val Ile Tyr Ser Ile Leu
 1               5                  10                  15
Val Cys Val Phe Gly Ser Ile Tyr Cys Leu Phe Ser Pro Arg Asn Pro
             20                  25                  30
Lys His Val Ala Thr Phe Gly His Met Phe Gly Arg Leu Ala Pro Leu
         35                  40                  45
Phe Gly Leu Lys Val Glu Cys Arg Lys Pro Ala Asp Ala Glu Asn Tyr
     50                  55                  60
Gly Asn Ala Ile Tyr Ile Ala Asn His Gln Asn Asn Tyr Asp Met Val
 65                  70                  75                  80
Thr Ala Ala Asn Ile Val Gln Pro Pro Thr Val Thr Val Gly Lys Lys
                 85                  90                  95
Ser Leu Leu Trp Ile Pro Phe Phe Gly Gln Leu Tyr Trp Leu Thr Gly
                100                 105                 110
Asn Leu Leu Ile Asp Arg Asn Asn Arg Ala Lys Ala His Ser Thr Ile
            115                 120                 125
Ala Ala Val Val Asn His Phe Lys Lys Arg Arg Ile Ser Ile Trp Met
        130                 135                 140
Phe Pro Glu Gly Thr Arg Ser Arg Gly Arg Gly Leu Leu Pro Phe Lys
145                 150                 155                 160
Thr Gly Ala Phe His Ala Ala Ile Ala Ala Gly Val Pro Ile Ile Pro
                165                 170                 175
Val Cys Val Ser Asn Thr Ser Asn Lys Val Asn Leu Asn Arg Leu Asn
            180                 185                 190
Asn Gly Leu Val Ile Val Glu Met Leu Pro Pro Val Asp Val Ser Glu
        195                 200                 205
Tyr Gly Lys Asp Gln Val Arg Glu Leu Ala Ala His Cys Arg Ala Leu
    210                 215                 220
Met Glu Gln Lys Ile Ala Glu Leu Asp Lys Glu Val Ala Glu Arg Glu
225                 230                 235                 240
Ala Thr Gly Lys Val
                245
```

( 2 ) INFORMATION FOR SEQ ID NO:5:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

TTTCCATATG A 11

( 2 ) INFORMATION FOR SEQ ID NO:6:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

TTCCCACATG A 11

( 2 ) INFORMATION FOR SEQ ID NO:7:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

TYTTCACATG Y 11

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

AGTAATCCAC AGAGCCAAAT G 21

( 2 ) INFORMATION FOR SEQ ID NO:9:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:9:

Val Leu Val Val Leu Ala Leu Ala Gly Cys Gly Phe Tyr Gly Val Ile
    1              5                      10                   15

Ala (2) INFORMATION FOR SEQ ID NO:10:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:10:

Arg Thr Cys Arg Tyr Asn Asn Asn Asn Asn Ala Cys Gly
1               5                   10

We claim:

1. An isolated DNA molecule comprising a nucleotide sequence as shown in SEQ ID NO:1 or mutant thereof encoding a functional acyltransferase.

2. A method for directing a fatty acid to the sn2 position of an acylglycerol lipid in a bacterial, yeast, or plant host comprising:

(a) transfecting the host with a vector containing an SLC1 gene or a mutant or portion thereof encoding a functional acyltransferase; and (b) allowing the SLC1 gene or mutant or portion thereof to be expressed in the host to direct the fatty acid to the sn2 position of the acylglycerol lipid.

3. The method according to claim 2 wherein said plant host is a food crop plant.

4. The method according to claim 2, wherein said vector comprises a promoter sequence including an 11 basepair inositol/choline-responsive element in the promoter having the consensus sequence TYTTCACATGY (SEQ ID NO:7).

5. The method according to claim 2 wherein said vector comprises a cauliflower mosaic virus (CaMV) 35S promoter sequence.

6. The method according to claim 2 wherein said vector comprises a human cytomegalovirus promoter sequence from a pcDNA3 or pRc/CMV vector.

7. A probe for detecting a DNA or RNA sequence homologous to the *Saccharomyces cerevisiae* gene SLC1 which probe contains a sense or antisense sequence to the nucleotide sequence as shown in SEQ ID NO:1 or a mutant thereof encoding a functional acyltransferase.

8. A probe according to claim 7 further comprising a detectable label.

9. A probe according to claim 8 wherein said detectable label is selected from the group consisting of chromophores, fluorophores, chemiluminescent materials and radioisotopes.

10. A probe according to claim 9 wherein said detectable label is a radioisotope.

\* \* \* \* \*